US009266839B2

(12) United States Patent
Hurd et al.

(10) Patent No.: US 9,266,839 B2
(45) Date of Patent: Feb. 23, 2016

(54) TRIFLUOROMETHYL PYRAZOLYL GUANIDINE $F_1F_0$-ATPASE INHIBITORS AND THERAPEUTIC USES THEREOF

(71) Applicant: Lycera Corporation, Ann Arbor, MI (US)

(72) Inventors: Alexander R. Hurd, Ann Arbor, MI (US); Clarke B. Taylor, Ann Arbor, MI (US); Jian Wang, Banchburg, NJ (US); Peng Zhou, Suzhou (CN)

(73) Assignee: Lycera Corporation, Ann Arbor, MI (US)

( * ) Notice: Subject to any disclaimer, the term of this patent is extended or adjusted under 35 U.S.C. 154(b) by 0 days.

(21) Appl. No.: 14/565,463

(22) Filed: Dec. 10, 2014

(65) Prior Publication Data

US 2015/0183745 A1 Jul. 2, 2015

Related U.S. Application Data

(60) Provisional application No. 61/979,619, filed on Apr. 15, 2014, provisional application No. 61/914,085, filed on Dec. 10, 2013.

(51) Int. Cl.
C07D 231/38 (2006.01)
A61K 31/415 (2006.01)
(52) U.S. Cl.
CPC ............ *C07D 231/38* (2013.01); *A61K 31/415* (2013.01)
(58) Field of Classification Search
CPC .......................... C07D 231/38; A61K 31/415
See application file for complete search history.

(56) References Cited

U.S. PATENT DOCUMENTS

| | | | |
|---|---|---|---|
| 4,977,189 A * | 12/1990 | Tomcufik et al. ............ 514/603 |
| 5,547,953 A | 8/1996 | Weichert et al. | |
| 6,916,813 B2 | 7/2005 | Atwal et al. | |
| 7,276,348 B2 | 10/2007 | Glick | |
| 8,324,258 B2 | 12/2012 | Glick et al. | |
| 8,431,604 B2 | 4/2013 | Netz et al. | |
| 8,481,576 B2 | 7/2013 | Netz et al. | |
| 8,497,307 B2 | 7/2013 | Glick et al. | |
| 9,000,014 B2 | 4/2015 | Glick et al. | |
| 2004/0009972 A1 | 1/2004 | Ding et al. | |
| 2004/0039033 A1 | 2/2004 | Atwal et al. | |
| 2004/0132750 A1 | 7/2004 | Kempson et al. | |
| 2006/0270741 A1 | 11/2006 | Durant et al. | |
| 2009/0163545 A1 | 6/2009 | Goldfarb | |
| 2009/0275099 A1 | 11/2009 | Glick | |
| 2010/0004227 A1 | 1/2010 | Glick | |
| 2010/0222400 A1 | 9/2010 | Glick et al. | |
| 2013/0324536 A1 | 12/2013 | Glick et al. | |
| 2013/0331392 A1 | 12/2013 | Hurd et al. | |
| 2014/0051727 A1 | 2/2014 | Glick et al. | |
| 2015/0119439 A1 | 4/2015 | Hurd et al. | |
| 2015/0148373 A1 | 5/2015 | Hurd et al. | |
| 2015/0152063 A1 | 6/2015 | Hurd et al. | |

FOREIGN PATENT DOCUMENTS

| | | |
|---|---|---|
| EP | 0659748 A1 | 6/1995 |
| EP | 1716127 A2 | 11/2006 |
| JP | 7188197 A | 7/1995 |
| WO | WO-00/47207 A1 | 8/2000 |
| WO | WO-01/05774 A1 | 1/2001 |
| WO | WO-02/02525 A2 | 1/2002 |
| WO | WO-03/045901 A2 | 6/2003 |
| WO | WO-03/050261 A2 | 6/2003 |
| WO | WO-03/106628 A2 | 12/2003 |
| WO | WO-2004/050610 A2 | 6/2004 |
| WO | WO-2005/082871 A2 | 9/2005 |
| WO | WO-2006/007532 A2 | 1/2006 |
| WO | WO-2006/073448 A2 | 7/2006 |
| WO | WO-2008/116156 A2 | 9/2008 |
| WO | WO-2009/036175 A2 | 3/2009 |
| WO | WO-2009/131384 A2 | 10/2009 |
| WO | WO-2010/030891 A2 | 3/2010 |
| WO | WO-2012/078867 A2 | 6/2012 |
| WO | WO-2012/078869 A1 | 6/2012 |
| WO | WO-2012/078874 A1 | 6/2012 |
| WO | WO-2013/185045 A1 | 12/2013 |
| WO | WO-2013/185046 A1 | 12/2013 |
| WO | WO-2013/185048 A2 | 12/2013 |
| WO | WO-2015/089149 A1 | 6/2015 |

OTHER PUBLICATIONS

AC1L8WR3—Compound Summary (CID 409375), Mar. 27, 2005, http://pubchem.ncbi.nlm.nih.gov/search/search.cgi.
Atwal et al., "N-[1-Aryl-2-(1-imidazolo)ethyl]-guanidine derivatives as potent inhibitors of the bovine mitochondrial $F_1F_0$ ATP hydrolase," *Bioorganic & Medicinal Chemistry Letters*, vol. 14, (2004), pp. 1027-1030.
Bisaha et al., "A switch in enantiomer preference between mitochondrial $F_1F_0$ -ATPase chemotypes," *Bioorganic & Medicinal Chemistry Letters*, vol. 15, (2005), pp. 2749-2751.
Blatt et al., "Bz-423 Superoxide Signals Apoptosis via Selective Activation of JNK, Bak, and Bax," *Free Radical Biology & Medicine*, pp. 1232-1242 (2008).
Brown et al., "ATP Synthase is Responsible for Maintaining Mitochondrial Membrane Potential in Bloodstream Form *Trypanosoma brucei*," *Eukaryotic Cell*, vol. 5, No. 1, (2006), pp. 45-53.
Comelli et al., "Downmodulation of mitochondrial $F_0F_1$ ATP synthase by diazoxide in cardiac myoblasts: a dual effect of the drug," *Am J Physiol Heart Circ Physiol*, vol. 292, (2007), pp. H820-H829.
Cunha et al., "Bismuth nitrate pentahydrate: a new and environmentally benign reagent for guanidylation of *N*-benzoylthioureas," *Tetrahedron Letters*, vol. 43 (2002), pp. 49-52.

(Continued)

*Primary Examiner* — Samantha Shterengarts
(74) *Attorney, Agent, or Firm* — Goodwin Procter LLP

(57) ABSTRACT

The invention provides trifluoromethyl pyrazolyl guanidine compounds that inhibit $F_1F_0$-ATPase, and methods of using trifluoromethyl pyrazolyl guanidine compounds as therapeutic agents to treat medical disorders, such as an immune disorder, inflammatory condition, or cancer.

53 Claims, 8 Drawing Sheets

(56) References Cited

OTHER PUBLICATIONS

Cunha et al., "Study of N-benzoyl-activation in the HgCl2-promoted Guanylation Reaction of Thioureas. Synthesis and Structural Analysis of N-benzoyl-guanidines," *Tetrahedron*, vol. 57, pp. 1671-1675, (2001).

Cunha et al., "The first bismuth(III)-catalyzed guanylation of thioureas," *Tetrahedron Letters*, vol. 47, (2006), pp. 6955-6956.

Cunha et al., "The first synthesis of pyridinium N-benzoylguanidines by bismuth- and mercury-promoted guanylation of N-iminopyridinium ylide with thioureas," *Tetrahedron*, vol. 61, (2005) pp. 10536-10540.

Database Registry on STN, RN 669724-32-7, RN 351226-10-3, and RN 330829-66-8, 3 pages.

Degliesposti et al., "Design and Discovery of Plasmepsin II Inhibitors Using an Automated Workflow on Large-Scale Grids," *ChemMedChem*, (2009), 4(7), pp. 1164-1173, Abstract.

Extended European Search Report for European Application No. EP11846398.3, dated Feb. 28, 2014, 5 pages.

Extended European Search Report for European Application No. EP11846595.4, dated Jun. 12, 2014, 6 pages.

Grover et al., "Excessive ATP hydrolysis in ischemic myocardium by mitochondrial $F_1F_0$ -ATPase: effect of selective pharmacological inhibition of mitochondrial ATPase hydrolase activity," *Am J Physiol, Heart Circ Physiol*, vol. 287, (2004), pp. H1747-H1755.

Hamann et al., "Benzodiazepine-based selective inhibitors of mitochondrial $F_1F_0$ ATP hydrolase," *Bioorg Med Chem Lett*, (2004), vol. 14, pp. 1031-1034, Abstract.

International Preliminary Report on Patentability of the International Bureau of WIPO, for International Application No. PCT/US2011/063943, dated Feb. 25, 2014, 5 pages.

International Search Report and Written Opinion for International Application No. PCT/US2014/069453 dated Mar. 23, 2015, 12 pages.

International Search Report and Written Opinion for International Application No. PCT/US2014/069487 dated Mar. 18, 2015, 7 pages.

International Search Report and Written Opinion for International Application No. PCT/US2014/069494, dated Feb. 5, 2015, 13 pages.

International Search Report and Written Opinion of the International Searching Authority, the Korean Intellectual Property Office, for International Application No. PCT/US2008/076021, dated Mar. 27, 2009, 8 pages.

International Search Report and Written Opinion of the International Searching Authority, the Korean Intellectual Property Office, for International Application No. PCT/US2009/056675, dated Apr. 14, 2010, 10 pages.

International Search Report and Written Opinion of the International Searching Authority, the U.S. Patent & Trademark Office, for International Application No. PCT/US2011/063943, dated Apr. 9, 2012, 7 pages.

International Search Report and Written Opinion of the International Searching Authority, the U.S. Patent & Trademark Office, for International Application No. PCT/US2011/063945, dated Apr. 18, 2012, 8 pages.

International Search Report and Written Opinion of the International Searching Authority, the U.S. Patent & Trademark Office, for International Application No. PCT/US2011/063950, dated Apr. 26, 2012, 8 pages.

International Search Report and Written Opinion of the International Searching Authority, the U.S. Patent & Trademark Office, for International Application No. PCT/US2013/044734, dated Nov. 20, 2013, 14 pages.

International Search Report and Written Opinion of the International Searching Authority, the U.S. Patent & Trademark Office, for International Application No. PCT/US2013/044736, dated Nov. 8, 2013, 13 pages.

International Search Report and Written Opinion of the International Searching Authority, the U.S. Patent & Trademark Office, for International Application No. PCT/US2013/044738, dated Nov. 20, 2013, 11 pages.

Ito et al., "A medium-term rat liver bioassay for rapid in vivo detection of carcinogenic potential of chemicals," *Cancer Sci*, (2003), vol. 94, No. 1, pp. 3-8.

Johnson et al., "Identification and Validation of the Mitochondrial $F_1F_0$ -ATPase as the Molecular Target of the Immunomodulatory Benzodiazepine Bz-423," Chemistry & Biology, vol. 12, pp. 485-496 (2005).

Kryl'skii, et al., "Arylbiguanides in Heterocyclization Reactions," *Russian Journal of General Chemistry*, vol. 75, No. 2, (2005), pp. 303-310.

Lübbers et al., "Design, Synthesis, and Structure-Activity Relationship Studies of ATP Analogues as DNA Gyrase Inhibitors," *Bioorganic & Medicinal Chemistry Letters*, vol. 10, (2000), pp. 821-826.

Schnaufer et al., "The $F_1$-ATP synthase complex in bloodstream stage trypanosomes has an unusual and essential function," *The European Molecular Biology Organization Journal*, vol. 24, (2005), pp. 4029-4040.

STN Search Transcript Registry/Caplus Databases, (2010) 108 pages.

STN Search Transcript Registry/Caplus Databases, (2010) 30 pages.

STN Search Transcript Registry/Caplus Databases, (2010) 85 pages.

STN Search Transcript Registry/Caplus Databases, (2012) 89 pages.

Wen-Li et al., "Inhibition of the Ecto-Beta Subunit of F1F0-ATPase Inhibits Proliferation and induces Apoptosis in Acute Myeloid Leukemia Cell Lines," Journal of Experimental & Clinical Cancer Research, vol. 31, pp. 1-9 (2012).

Williams et al., "Identification of Compounds that Bind Mitochondrial F1F0 ATPase by Screening a Triazine Library for Correction of Albinism," *Chemistry & Biology*, vol. 11, (2004), pp. 1251-1259.

\* cited by examiner

TRIFLUOROMETHYL PYRAZOLYL GUANIDINE $F_1F_0$-ATPASE INHIBITORS AND THERAPEUTIC USES THEREOF

CROSS REFERENCE TO RELATED APPLICATIONS

This application claims the benefit of and priority to U.S. Provisional Patent Application Ser. No. 61/914,085, filed Dec. 10, 2013, and U.S. Provisional Patent Application Ser. No. 61/979,619, filed Apr. 15, 2014; the contents of each of which are hereby incorporated by reference.

FIELD OF THE INVENTION

The invention provides inhibitors of $F_1F_0$-ATPases (e.g., mitochondrial $F_1F_0$-ATPases) and their therapeutic use. In particular, the invention provides trifluoromethyl pyrazolyl guanidine compounds that inhibit $F_1F_0$-ATPase, and methods of using trifluoromethyl pyrazolyl guanidine compounds as therapeutic agents to treat a number of medical conditions.

BACKGROUND

Multicellular organisms exert precise control over cell number. A balance between cell proliferation and cell death achieves this homeostasis. Cell death occurs in nearly every type of vertebrate cell via necrosis or through a suicidal form of cell death, known as apoptosis. Apoptosis is triggered by a variety of extracellular and intracellular signals that engage a common, genetically programmed death mechanism.

Multicellular organisms use apoptosis to instruct damaged or unnecessary cells to destroy themselves for the good of the organism. Control of the apoptotic process therefore is very important to normal development, for example, fetal development of fingers and toes requires the controlled removal, by apoptosis, of excess interconnecting tissues, as does the formation of neural synapses within the brain. Similarly, controlled apoptosis is responsible for the sloughing off of the inner lining of the uterus (the endometrium) at the start of menstruation. While apoptosis plays an important role in tissue sculpting and normal cellular maintenance, it is also a component of the primary defense against cells and invaders (e.g., viruses) which threaten the well being of the organism.

Many diseases are associated with dysregulation of apoptotic cell death. Experimental models have established a cause-effect relationship between aberrant apoptotic regulation and the pathogenicity of various neoplastic, autoimmune and viral diseases. For instance, in the cell-mediated immune response, effector cells (e.g., cytotoxic T lymphocytes "CTLs") destroy virus-infected cells by inducing the infected cells to undergo apoptosis. The organism subsequently relies on the apoptotic process to destroy the effector cells when they are no longer needed. Autoimmunity is normally prevented by the CTLs inducing apoptosis in each other and even in themselves. Defects in this process are associated with a variety of immune diseases such as lupus erythematosus and rheumatoid arthritis.

Multicellular organisms also use apoptosis to instruct cells with damaged nucleic acids (e.g., DNA) to destroy themselves prior to becoming cancerous. Some cancer-causing viruses overcome this safeguard by reprogramming infected (transformed) cells to abort the normal apoptotic process. For example, several human papilloma viruses (HPVs) have been implicated in causing cervical cancer by suppressing the apoptotic removal of transformed cells by producing a protein (E6) which inactivates the p53 apoptosis promoter. Similarly, the Epstein-Barr virus (EBV), the causative agent of mononucleosis and Burkitt's lymphoma, reprograms infected cells to produce proteins that prevent normal apoptotic removal of the aberrant cells thus allowing the cancerous cells to proliferate and to spread throughout the organism.

Still other viruses destructively manipulate a cell's apoptotic machinery without directly resulting in the development of a cancer. For example, destruction of the immune system in individuals infected with the human immunodeficiency virus (HIV) is thought to progress through infected $CD4^+$ T cells (about 1 in 100,000) instructing uninfected sister cells to undergo apoptosis.

Some cancers that arise by non-viral means have also developed mechanisms to escape destruction by apoptosis. Melanoma cells, for instance, avoid apoptosis by inhibiting the expression of the gene encoding Apaf-1. Other cancer cells, especially lung and colon cancer cells, secrete high levels of soluble decoy molecules that inhibit the initiation of CTL mediated clearance of aberrant cells. Faulty regulation of the apoptotic machinery has also been implicated in various degenerative conditions and vascular diseases.

Controlled regulation of the apoptotic process and its cellular machinery is important to the survival of multicellular organisms. Typically, the biochemical changes that occur in a cell instructed to undergo apoptosis occur in an orderly procession. However, as shown above, flawed regulation of apoptosis can cause serious deleterious effects in the organism.

The need exists for improved compositions and methods for regulating the apoptotic processes in subjects afflicted with diseases and conditions characterized by faulty regulation of these processes (e.g., viral infections, hyperproliferative autoimmune disorders, chronic inflammatory conditions, and cancers). The present invention addresses this need and provides other related advantages.

SUMMARY

The invention provides trifluoromethyl pyrazolyl guanidine compounds that inhibit $F_1F_0$-ATPase (e.g., mitochondrial $F_1F_0$-ATPase), pharmaceutical compositions comprising trifluoromethyl pyrazolyl guanidine compounds, and methods of using such compounds and pharmaceutical compositions to treat a number of medical conditions. The invention relates in part to the discovery of compositions having surprising superior pharmaceutical properties. For example, the compound 3-chloro-N-(((3-chloro-5-fluorophenyl)amino)((5-(trifluoromethyl)-1H-pyrazol-3-yl)amino)methylene)benzamide (Compound 1) was surprisingly discovered to have reduced off-target effects compared to 3-chloro-N-(((3-chlorophenyl)amino)((5-(trifluoromethyl)-1H-pyrazol-3-yl)amino)methylene)benzamide (Compound 2). For instance, Compound 1 was surprisingly discovered to be approximately 3-fold less potent towards Cytochrome P450 2D6 enzyme compared to Compound 2. The reduced potency of Compound 1 to Cytochrome P450 2D6 enzyme improves the safety profile of the compound in patients taking additional medication, either as part of a combination therapy with Compound 1 to treat a medical disorder described herein or for the treatment of a different ailment. Other advantages and benefits of the compositions and methods are described in, for example, the detailed description and Examples.

Accordingly, one aspect of the invention provides a family of compounds represented by Formula I:

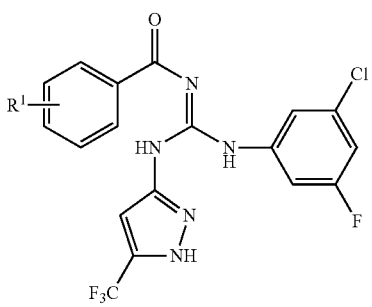

(I)

or a geometric isomer or tautomer; or a pharmaceutically acceptable salt or solvate of any of the foregoing; wherein $R^1$ is a chloro group located at either the meta-position or para-position of the phenyl group to which it is attached.

Another aspect of the invention provides a compound represented by:

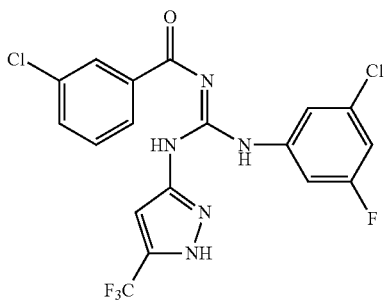 [SMILES: O=C(/N=C(/Nc1cc(F)cc(Cl)c1)Nc1cc(C(F)(F)F)[nH]n1)c1cccc(Cl)c1]

or a geometric isomer or tautomer; or a pharmaceutically acceptable salt of any of the foregoing.

Another aspect of the invention provides a compound represented by:

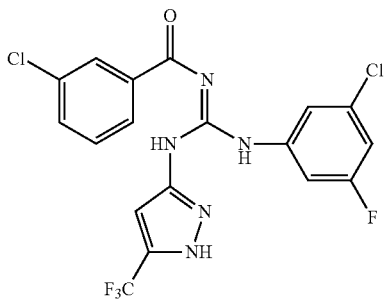 [SMILES: O=C(/N=C(/Nc1cc(F)cc(Cl)c1)Nc1cc(C(F)(F)F)[nH]n1)c1cccc(Cl)c1]

or a geometric isomer or tautomer; or a solvate of any of the foregoing.

The invention also provides compounds in crystalline form. For example, one aspect of the invention provides crystalline compound 3-chloro-N-(((3-chloro-5-fluorophenyl) amino) ((5-(trifluoromethyl)-1H-pyrazol-3-yl)amino)methylene)benzamide. In certain embodiments, the crystalline compound 3-chloro-N-(((3-chloro-5-fluorophenyl)amino) ((5-(trifluoromethyl)-1H-pyrazol-3-yl)amino)methylene) benzamide is in polymorphic Form I, which exhibits an X-ray powder diffraction pattern comprising peaks at the following diffraction angles (2θ): 6.2±0.2, 7.1±0.2, 9.4±0.2, 10.7±0.2, 15.6±0.2, 19.0±0.2, 20.0±0.2, and 25.2±0.2. In certain other embodiments, the crystalline compound 3-chloro-N-(((3-chloro-5-fluorophenyl)amino)((5-(trifluoromethyl)-1H-pyrazol-3-yl)amino)methylene)benzamide is in polymorphic Form II, which exhibits an X-ray powder diffraction pattern comprising peaks at the following diffraction angles (2θ): 6.3±0.2, 7.3±0.2, 11.0±0.2, 12.8±0.2, 16.9±0.2, 19.2±0.2, 20.6±0.2, 22.2±0.2, 25.7±0.2, 26.0±0.2, and 35.7±0.2.

Another aspect of the invention provides crystalline compound 3-chloro-N-(((3-chloro-5-fluorophenyl)amino)((5-(trifluoromethyl)-1H-pyrazol-3-yl)amino)methylene)benzamide acetone solvate. In certain embodiments, the crystalline compound 3-chloro-N-(((3-chloro-5-fluorophenyl)amino) ((5-(trifluoromethyl)-1H-pyrazol-3-yl)amino)methylene) benzamide acetone solvate exhibits an X-ray powder diffraction pattern comprising peaks at the following diffraction angles (2θ): 6.2±0.2, 8.3±0.2, 14.7±0.2, 17.5±0.2, 17.9±0.2, 18.5±0.2, 20.2±0.2, 20.9±0.2, 23.5±0.2, and 25.9±0.2.

The foregoing compounds can be present in a pharmaceutical composition comprising a compound described herein and a pharmaceutically acceptable carrier.

Another aspect of the invention provides a method of treating a subject suffering from a medical disorder. The method comprises administering to the subject a therapeutically effective amount of one or more trifluoromethyl pyrazolyl guanidine compounds described herein, e.g., a compound of Formula I or one of the crystalline forms described herein, in order to ameliorate a symptom of the disorder. A large number of disorders can be treated using the trifluoromethyl pyrazolyl guanidine compounds described herein. For example, the compounds described herein can be used to treat an immune disorder or inflammatory disorder, such as rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, epidermal hyperplasia, and other medical disorders described herein. The compounds described herein can also be used to treat a cardiovascular disease, myeloma, lymphoma, cancer, or bacterial infection.

Another aspect of the invention provides a method of inhibiting an $F_1F_0$-ATPase, for example, a mitochondrial $F_1F_0$-ATPase. The method comprises exposing the $F_1F_0$-ATPase to a compound described herein, e.g., a compound of Formula I or one of the crystalline forms described herein, to inhibit said $F_1F_0$-ATPase.

DETAILED DESCRIPTION OF THE INVENTION

Figure 1:
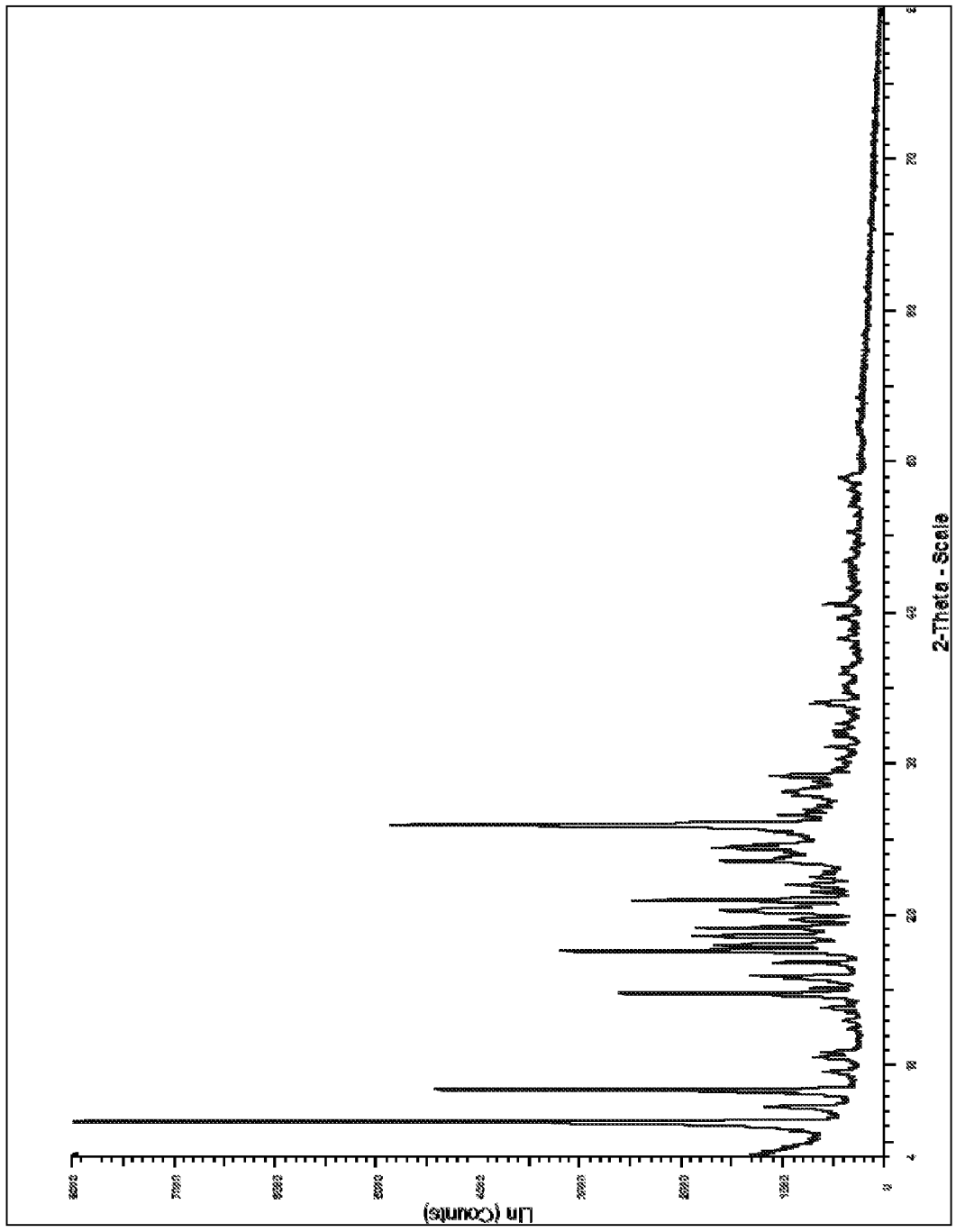
FIG. 1 is an X-ray powder diffractogram of 3-chloro-N-(((3-chloro-5-fluorophenyl)amino)((5-(trifluoromethyl)-1H-pyrazol-3-yl)amino)methylene)benzamide acetone solvate, as further described in Example 2.

The invention provides trifluoromethyl pyrazolyl guanidine compounds that inhibit $F_1F_0$-ATPase (e.g., mitochondrial $F_1F_0$-ATPase), pharmaceutical compositions comprising the trifluoromethyl pyrazolyl guanidine compounds, and methods of using the trifluoromethyl pyrazolyl guanidine compounds and pharmaceutical compositions in therapy. As explained in part above, one aspect of the invention pertains to the discovery of compositions having surprising superior pharmaceutical properties. For example, the compound 3-chloro-N-(((3-chloro-5-fluorophenyl)amino)((5-(trifluoromethyl)-1H-pyrazol-3-yl)amino)methylene)benzamide (Compound 1) was surprisingly discovered to have reduced off-target effects compared to 3-chloro-N-(((3-chlorophenyl)amino)((5-(trifluoromethyl)-1H-pyrazol-3-yl)amino)methylene)benzamide (Compound 2). For instance, Compound 1 was surprisingly discovered to be approximately 3-fold less potent towards Cytochrome P450 2D6 enzyme compared to Compound 2.

The reduced potency of Compound 1 to Cytochrome P450 2D6 enzyme improves the safety profile of the compound in patients taking additional medication, either as part of a combination therapy with Compound 1 to treat a medical disorder described herein or for the treatment of a different ailment. Cytochrome P450 2D6 is involved in the metabolism of many therapeutic agents. Inhibiting the action of Cytochrome P450 2D6 is undesirable because such inhibition can alter the rate of metabolism of a therapeutic agent causing an otherwise safe dosing amount or frequency to become unsafe for the patient. The present invention provides compositions with reduced affects on the Cytochrome P450 2D6 enzyme, thereby providing a therapeutic with an improved safety profile when administered to patients taking other medication.

Exemplary compositions and methods of the present invention are described in more detail in the following sections: I. Modulators of $F_1F_0$-ATPase Activity; II. Trifluoromethyl Pyrazolyl Guanidine Compounds; III. Therapeutic Applications of Trifluoromethyl Pyrazolyl Guanidine Compounds, and IV. Pharmaceutical Compositions, Formulations, and Exemplary Administration Routes and Dosing Considerations. Aspects of the invention described in one particular section are not to be limited to any particular section.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as "Comprehensive Organic Synthesis" (B. M. Trost & I. Fleming, eds., 1991-1992); "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

To facilitate an understanding of the present invention, a number of terms and phrases are defined below.

As used herein, the term "guanidine" refers to a compound having the following core structure:

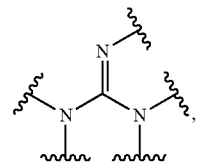 [SMILES: *N=C(N(*)*)N(*)*]

including pharmaceutically acceptable salt forms. The symbol "⌇⌇⌇" indicates a point of attachment.

Compounds of the disclosure may contain one or more double bonds and, therefore, exist as geometric isomers. Unless indicated otherwise, generic chemical structures and graphical representations of specific compounds encompass all geometric isomers. The present invention encompasses the various geometric isomers and mixtures thereof resulting from the arrangement of substituents around a double bond (e.g., a carbon-carbon double bond, or a carbon-nitrogen double bond). Substituents around a double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a double bond alternatively can be referred to as "cis" or "trans," where "cis" represents substituents on the same side of the double bond and "trans" represents substituents on opposite sides of the double bond.

Certain compounds described herein may exist as a single tautomer or as a mixture of tautomers. For example, certain guanidine compounds having a hydrogen atom attached to at least one of the guanidine nitrogen atoms can exist as a single tautomer or a mixture of tautomers. To illustrate, depending upon the substituents attached at the $R^1$, $R^2$ and $R^3$ positions, the guanidine compound may exist as a single tautomer represented by A, B, or C, or as mixture of two or more of A, B, and C.

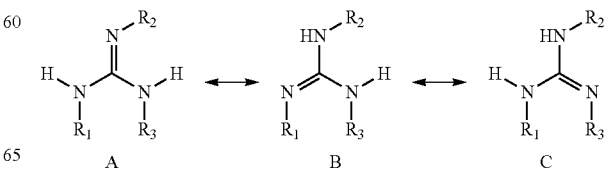

The compounds disclosed herein can exist in solvated as well as unsolvated forms with pharmaceutically acceptable solvents such as water, ethanol, acetone, and the like, and it is intended that the invention embrace both solvated and unsolvated forms.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$ $^{31}P$, $^{32}P$, $^{35}S$, $^{18}F$ and $^{36}Cl$, respectively.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in, for instance, Examples herein, by substituting an isotopically labeled reagent for a non-isotopically labeled reagent.

The chemical name "3-chloro-N-(((3-chloro-5-fluorophenyl)amino)((5-(trifluoromethyl)-1H-pyrazol-3-yl)amino) methylene)benzamide" refers to the following compound:

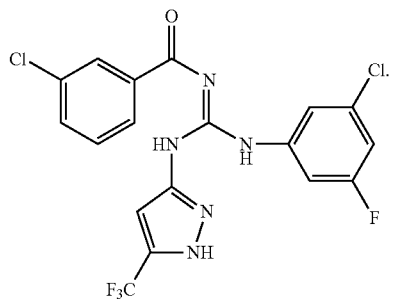 [SMILES: O=C(/N=C(/Nc1cc(F)cc(Cl)c1)Nc1cc(C(F)(F)F)[nH]n1)c1cccc(Cl)c1]

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The term "$IC_{50}$" is art-recognized and refers to the concentration of a compound that is required for 50% inhibition of its target.

The term "$EC_{50}$" is art-recognized and refers to the concentration of a compound at which 50% of its maximal effect is observed.

The terms "subject" and "patient" refer to organisms to be treated by the methods of the present invention. Such organisms preferably include, but are not limited to, mammals (e.g., murines, simians, equines, bovines, porcines, canines, felines, and the like), and most preferably includes humans. In the context of the invention, the terms "subject" and "patient" generally refer to an individual who will receive or who has received treatment (e.g., administration of a compound of the present invention and optionally one or more other agents) for a condition characterized by the dysregulation of apoptotic processes.

As used herein, the term "effective amount" refers to the amount of a compound sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

The phrase "pathologically proliferating or growing cells" refers to a localized population of proliferating cells in an animal that is not governed by the usual limitations of normal growth.

As used herein, the term "un-activated target cell" refers to a cell that is either in the $G_o$ phase or one to which a stimulus has not been applied.

As used herein, the term "activated target lymphoid cell" refers to a lymphoid cell that has been primed with an appropriate stimulus to cause a signal transduction cascade, or alternatively, a lymphoid cell that is not in $G_o$ phase. Activated lymphoid cells may proliferate, undergo activation induced cell death, or produce one or more cytotoxins, cytokines, or other related membrane-associated proteins characteristic of the cell type (e.g., $CD8^+$ or $CD4^+$). They are also capable of recognizing and binding any target cell that displays a particular antigen on its surface, and subsequently releasing its effector molecules.

As used herein, the term "activated cancer cell" refers to a cancer cell that has been primed with an appropriate stimulus to cause signal transduction. An activated cancer cell may or may not be in the $G_O$ phase.

An activating agent is a stimulus that upon interaction with a target cell results in a signal transduction cascade. Examples of activating stimuli include, but are not limited to, small molecules, radiant energy, and molecules that bind to cell activation cell surface receptors. Responses induced by activation stimuli can be characterized by changes in, among others, intracellular $Ca^{2+}$, superoxide, or hydroxyl radical levels; the activity of enzymes like kinases or phosphatases; or the energy state of the cell. For cancer cells, activating agents also include transforming oncogenes.

As used herein, the term "dysregulation of the process of cell death" refers to any aberration in the ability (e.g., predisposition) of a cell to undergo cell death via either necrosis or apoptosis. Dysregulation of cell death is associated with or induced by a variety of conditions, including for example, immune disorders (e.g., systemic lupus erythematosus, autoimmune disorders, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes, papilloma, HIV), and other conditions such as osteoarthritis and atherosclerosis.

It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

A "hyperproliferative disorder" as used herein refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A metastatic cell or tissue means that the cell can invade and destroy neighboring body structures. Hyperplasia is a form of cell proliferation involving an increase in cell number in a tissue or organ, without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium.

The pathological growth of activated lymphoid cells often results in an immune disorder or a chronic inflammatory condition. As used herein, the term "immune disorder" refers to any condition in which an organism produces antibodies or immune cells which recognize the organism's own molecules, cells or tissues. Non-limiting examples of immune disorders include autoimmune disorders, immune hemolytic anemia, immune hepatitis, Berger's disease or IgA nephropathy, Celiac Sprue, chronic fatigue syndrome, Crohn's disease, dermatomyositis, fibromyalgia, graft-versus-host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjorgren syndrome, systemic lupus erythematosus, type 1 diabetes, ulcerative colitis, vitiligo, tuberculosis, and the like.

As used herein, the term "chronic inflammatory condition" refers to a condition wherein the organism's immune cells are activated. Such a condition is characterized by a persistent inflammatory response with pathologic sequelae. This state is characterized by infiltration of mononuclear cells, proliferation of fibroblasts and small blood vessels, increased connective tissue, and tissue destruction. Examples of chronic inflammatory diseases include, but are not limited to, Crohn's disease, psoriasis, chronic obstructive pulmonary disease, inflammatory bowel disease, multiple sclerosis, and asthma. Immune diseases such as rheumatoid arthritis and systemic lupus erythematosus can also result in a chronic inflammatory state.

As used herein, the term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "modulate" refers to the activity of a compound (e.g., a compound of the present invention) to affect (e.g., to promote or retard) an aspect of cellular function, including, but not limited to, cell growth, proliferation, apoptosis, and the like.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Modulators of $F_1F_0$-ATPase Activity

In some embodiments, the present invention regulates $F_1F_0$-ATPase activity (e.g., mitochondrial $F_1F_0$-ATPase activity) through the exposure of cells to compounds of the present invention. In some embodiments, the compounds inhibit ATP synthesis and ATP hydrolysis. The effect of the compounds can be measured by detecting any number of cellular changes. For example, mitochondrial $F_1F_0$-ATPase activity and/or cell death may be assayed as described herein and in the art. In some embodiments, cell lines are maintained under appropriate cell culturing conditions (e.g., gas ($CO_2$), temperature and media) for an appropriate period of time to attain exponential proliferation without density dependent constraints. Cell number and or viability are measured using standard techniques, such as trypan blue exclusion/hemocytometry, or an Alamar Blue or MTT dye conversion assay. Alternatively, the cell may be analyzed for the expression of genes or gene products associated with aberrations in apoptosis or necrosis.

In some embodiments, exposing the compounds of the present invention to a cell induces apoptosis. In certain other embodiments, the present invention induces apoptosis or arrest of cell proliferation through interacting with the mitochondrial $F_1F_0$-ATPase. In yet other embodiments, compounds of the present invention cause an initial increase in cellular ROS levels (e.g., $O_2^-$) when administered to a subject.

II. Trifluoromethyl Pyrazolyl Guanidine Compounds

One aspect of the invention provides a family of compounds represented by Formula I:

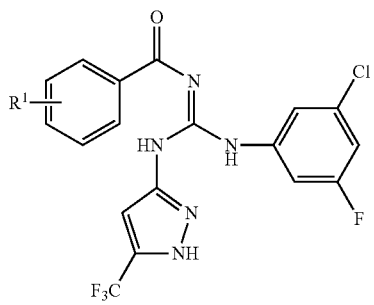

(I)

or geometric isomer or tautomer; or a pharmaceutically acceptable salt or solvate of any of the foregoing; wherein $R^1$ is a chloro group located at either the meta-position or para-position of the phenyl group to which it is attached. It is understood that the terms "meta" and "para" refer to 3-position and 4-position, respectively, of the phenyl group with the 1-position being the point of attachment to the carbonyl.

In certain embodiments, the compound is a compound of Formula I or a geometric isomer or tautomer, or a pharmaceutically acceptable salt of any of the foregoing. In certain other embodiments, the compound is a compound of Formula I or a geometric isomer or tautomer, or a solvate of any of the foregoing. In certain embodiments, the compound is in the form of an acetone solvate.

In certain embodiments, the compound is represented by:

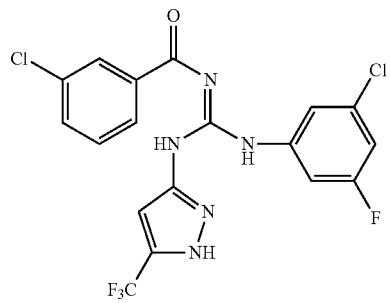 [SMILES: O=C(/N=C(/Nc1cc(F)cc(Cl)c1)Nc1cc(C(F)(F)F)[nH]n1)c1cccc(Cl)c1]

or a geometric isomer or tautomer; or a pharmaceutically acceptable salt of any of the foregoing. In certain other embodiments, the compound is represented by:

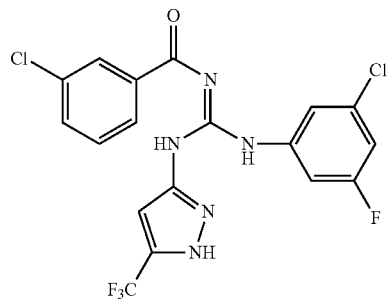 [SMILES: O=C(/N=C(/Nc1cc(F)cc(Cl)c1)Nc1cc(C(F)(F)F)[nH]n1)c1cccc(Cl)c1]

or a geometric isomer or tautomer; or a solvate of any of the foregoing. In certain embodiments, the compound is in the form of an acetone solvate.

In yet other embodiments, the compound is represented by:

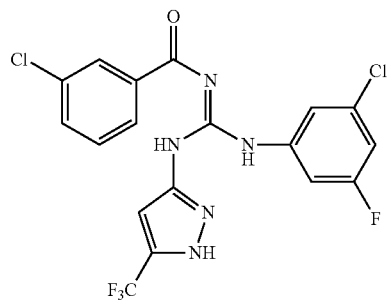 [SMILES: O=C(/N=C(/Nc1cc(F)cc(Cl)c1)Nc1cc(C(F)(F)F)[nH]n1)c1cccc(Cl)c1]

or a geometric isomer or tautomer. In still other embodiments, the compound is represented by:

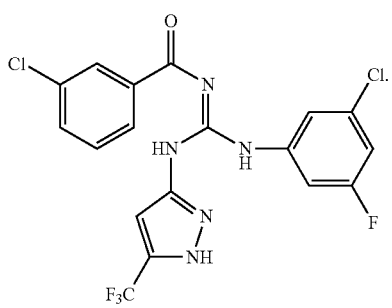 [SMILES: O=C(/N=C(/Nc1cc(F)cc(Cl)c1)Nc1cc(C(F)(F)F)[nH]n1)c1cccc(Cl)c1]

Another aspect of the invention provides a compound represented by:

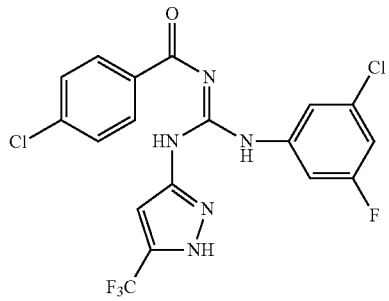 [SMILES: O=C(/N=C(/Nc1cc(F)cc(Cl)c1)Nc1cc(C(F)(F)F)[nH]n1)c1ccc(Cl)cc1]

or a geometric isomer or tautomer; or a pharmaceutically acceptable salt or solvate of any of the foregoing. In certain embodiments, the compound is

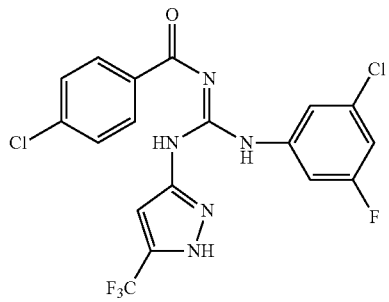 [SMILES: O=C(/N=C(/Nc1cc(F)cc(Cl)c1)Nc1cc(C(F)(F)F)[nH]n1)c1ccc(Cl)cc1]

or a geometric isomer or tautomer; or a pharmaceutically acceptable salt of any of the foregoing.

In certain certain other embodiments, the compound is

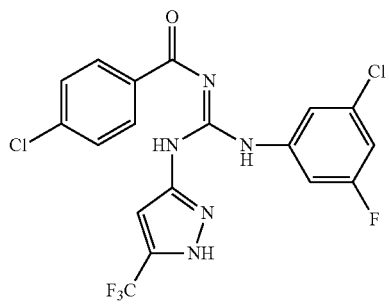

or a geometric isomer or tautomer; or a solvate of any of the foregoing. In yet other embodiments, the compound is

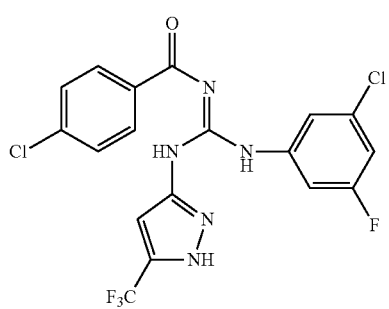 [SMILES: O=C(/N=C(/Nc1cc(F)cc(Cl)c1)Nc1cc(C(F)(F)F)[nH]n1)c1ccc(Cl)cc1]

or a geometric isomer or tautomer. In still other embodiments, the compound is

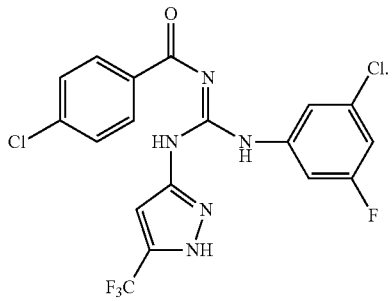 [SMILES: O=C(/N=C(/Nc1cc(F)cc(Cl)c1)Nc1cc(C(F)(F)F)[nH]n1)c1ccc(Cl)cc1]

Crystalline Forms of Compounds

Another aspect of the invention provides compounds in crystalline form. For example, another aspect of the invention provides crystalline compound 3-chloro-N-(((3-chloro-5-fluorophenyl)amino)((5-(trifluoromethyl)-1H-pyrazol-3-yl)amino)methylene)benzamide. This crystalline compound can be in different polymeric forms. For example, polymorphic Form I and polymorphic Form II have been discovered.

A. Crystalline Form I of 3-Chloro-N-(((3-chloro-5-fluorophenyl)amino)((5-(trifluoromethyl)-1H-pyrazol-3-yl)amino)methylene)benzamide Procedures for making crystalline Form I of 3-chloro-N-(((3-chloro-5-fluorophenyl)amino)((5-(trifluoromethyl)-1H-pyrazol-3-yl)amino)methylene)benzamide are described in, for instance, Example 3 herein. An X-ray powder diffractogram of Form I is provided in FIG. 3. A differential scanning calorimetry curve of Form I is provided in FIG. 4, along with a thermal gravimetric analysis curve of Form I. Form I of 3-chloro-N-(((3-chloro-5-fluorophenyl)amino)((5-(trifluoromethyl)-1H-pyrazol-3-yl)amino)methylene)benzamide can be characterized according its X-ray powder diffractogram and its melting point onset as determined by differential scanning calorimetry.

Accordingly, one aspect of the invention provides a crystalline 3-chloro-N-(((3-chloro-5-fluorophenyl)amino)((5-(trifluoromethyl)-1H-pyrazol-3-yl)amino)methylene)benzamide exhibiting an X-ray powder diffraction pattern comprising peaks at the following diffraction angles (2θ): 6.2±0.2, 7.1±0.2, 9.4±0.2, 10.7±0.2, 15.6±0.2, 19.0±0.2, 20.0±0.2, and 25.2±0.2. In certain embodiments, the relative intensity of the peak at said diffraction angles (2θ) is at least 20%. In certain embodiments, the relative intensity of the peak at said diffraction angles (2θ) is at least 30%.

The crystalline compound may be further characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
|---|---|---|
| 6.2 | 14.3 | 53.8 |
| 7.1 | 12.4 | 69.6 |
| 9.4 | 9.4 | 53.8 |
| 10.7 | 8.3 | 51.0 |
| 12.9 | 6.9 | 34.6 |
| 15.6 | 5.7 | 92.8 |
| 16.4 | 5.4 | 29.1 |
| 17.9 | 4.9 | 44.0 |

-continued

| Angle [2θ] | d-spacing [Å] | Relative Intensity [%] |
|---|---|---|
| 19.0 | 4.7 | 100.0 |
| 20.0 | 4.4 | 62.6 |
| 21.9 | 4.1 | 38.9 |
| 23.6 | 3.8 | 51.4 |
| 25.2 | 3.5 | 57.8 |
| 27.3 | 3.3 | 24.0 |
| 28.4 | 3.1 | 15.8 |
| 35.0 | 2.6 | 10.0 |

Figure 3:
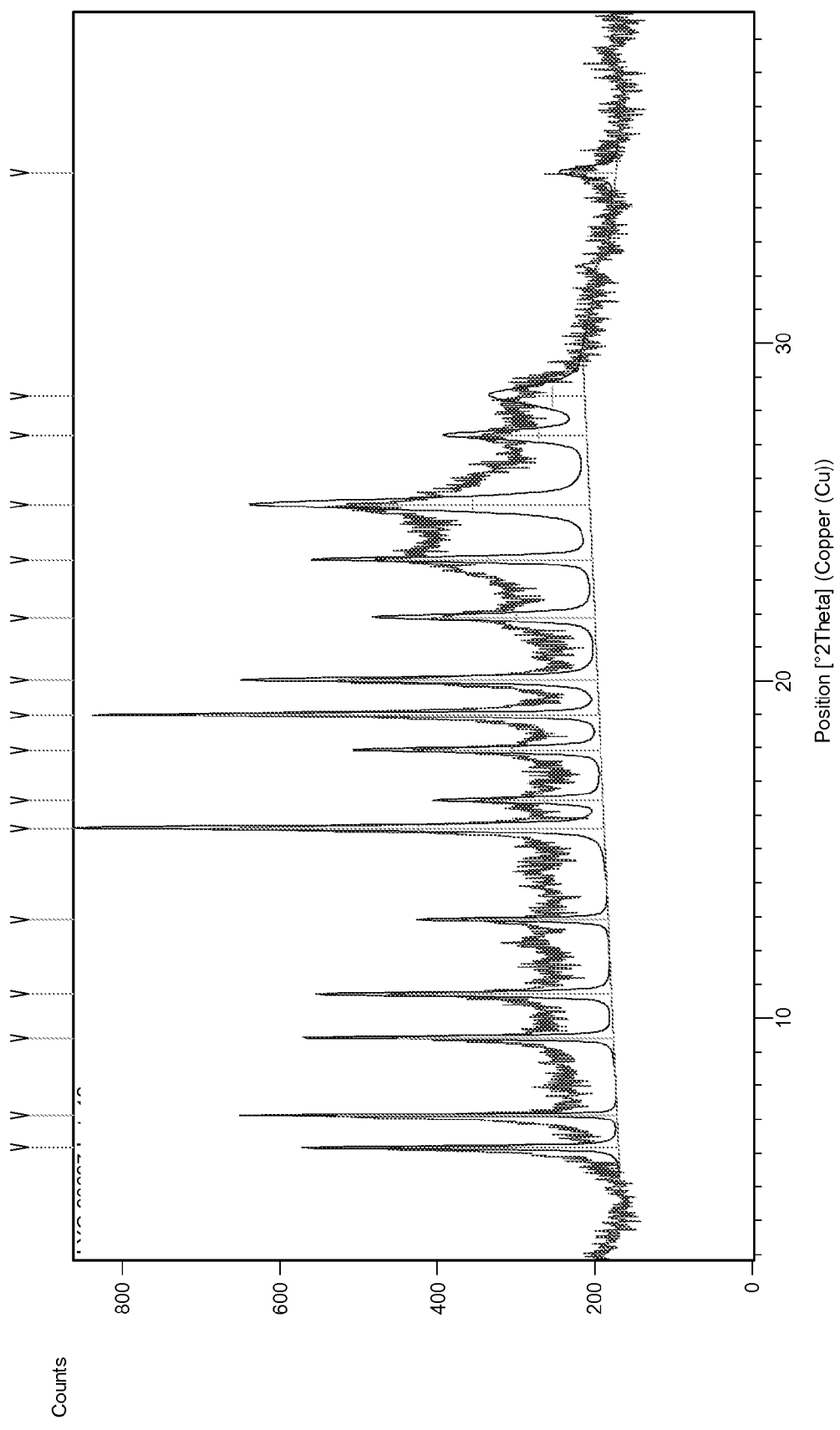
FIG. 3 is an X-ray powder diffractogram of crystalline Form I of 3-chloro-N-(((3-chloro-5-fluorophenyl)amino)((5-(trifluoromethyl)-1H-pyrazol-3-yl)amino)methylene)benzamide, as further described in Example 3.

In still further embodiments, crystalline Form I may be further characterized as having an X-ray powder diffraction pattern substantially as shown in FIG. 3.

An X-ray powder diffraction pattern may be obtained using CuKα radiation. The temperature at which the X-ray powder diffraction pattern is obtained may be, for example, 25±2 degrees Celsius.

Figure 4:
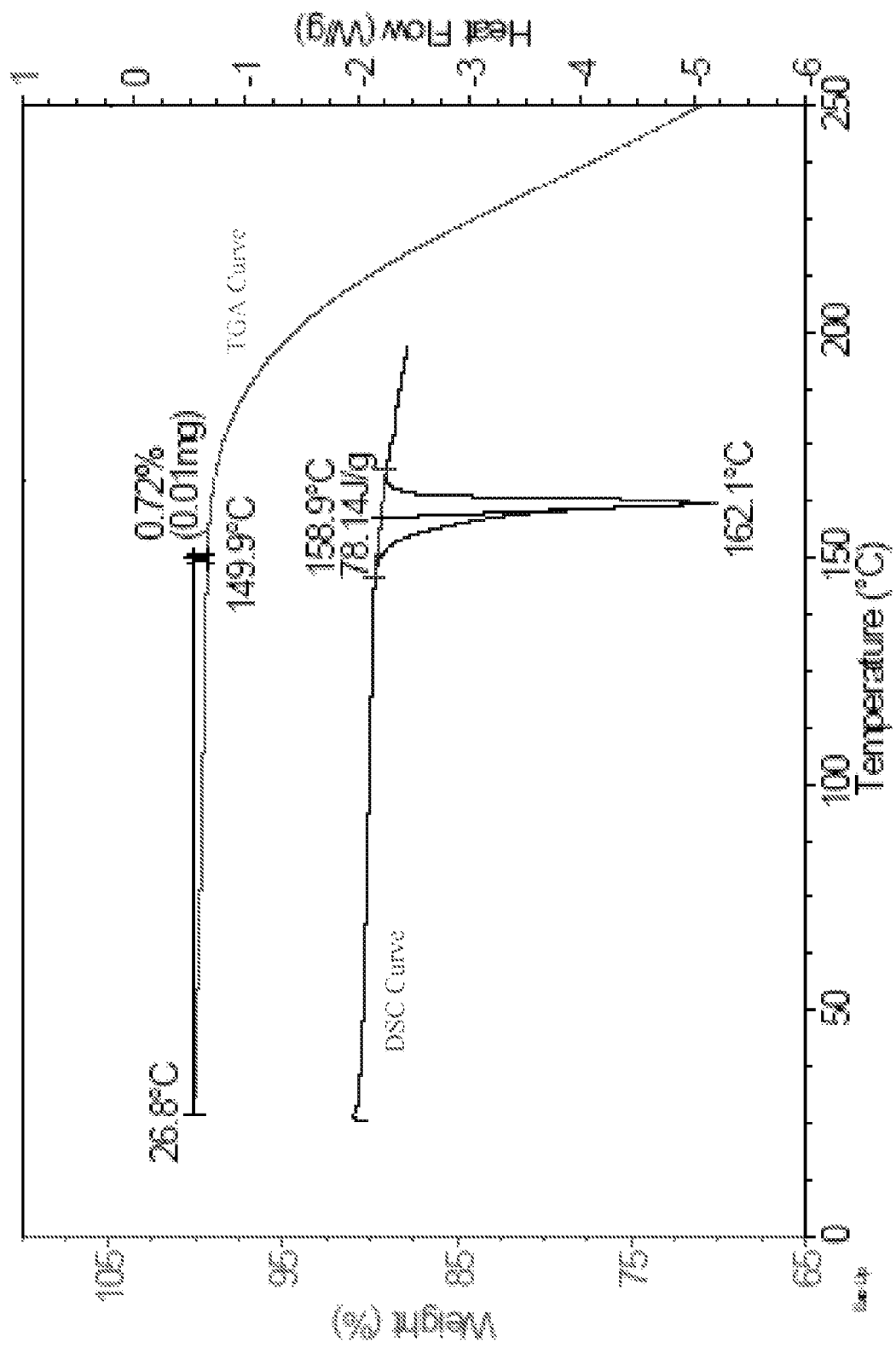
FIG. 4 is a differential scanning calorimetry curve (DSC) of crystalline Form I of 3-chloro-N-(((3-chloro-5-fluorophenyl)amino)((5-(trifluoromethyl)-1H-pyrazol-3-yl)amino)
methylene)benzamide, along with a thermal gravimetric
analysis (TGA) curve of crystalline Form I of 3-chloro-N-
(((3-chloro-5-fluorophenyl)amino)((5-(trifluoromethyl)-
1H-pyrazol-3-yl)amino)methylene)benzamide, each as further described in Example 3.

Crystalline Form I may be further characterized by its temperature of melting point onset as determined by differential scanning calorimetry. In certain embodiments, the crystalline compound has a melting point onset as determined by differential scanning calorimetry in the range of from about 149 degrees Celsius to about 164 degrees Celsius. In certain other embodiments, the crystalline compound has a melting point onset as determined by differential scanning calorimetry in the range of from about 157 degrees Celsius to about 161 degrees Celsius. In yet other embodiments, the crystalline compound has a melting point onset as determined by differential scanning calorimetry at about 159 degrees Celsius. Further yet, crystalline Form I may be further characterized by having a differential scanning calorimetry curve substantially the same as shown in FIG. 4.

B. Crystalline Form II of 3-Chloro-N-(((3-chloro-5-fluorophenyl)amino)((5-(trifluoromethyl)-1H-pyrazol-3-yl)aminomethylene)benzamide Procedures for making crystalline Form II of 3-chloro-N-(((3-chloro-5-fluorophenyl)amino)((5-(trifluoromethyl)-1H-pyrazol-3-yl)amino)methylene)benzamide are described in, for instance, Examples 4 and 5 herein. Exemplary X-ray powder diffractograms of crystalline Form II are provided in FIGS. 5 and 7. Differential scanning calorimetry curves of crystalline Form II are provided in FIGS. 6 and 8. Crystalline Form II of 3-chloro-N-(((3-chloro-5-fluorophenyl)amino)((5-(trifluoromethyl)-1H-pyrazol-3-yl)amino)methylene)benzamide can be characterized according its X-ray powder diffractogram and its melting point onset as determined by differential scanning calorimetry.

Accordingly, one aspect of the invention provides a crystalline 3-chloro-N-(((3-chloro-5-fluorophenyl)amino)((5-(trifluoromethyl)-1H-pyrazol-3-yl)amino)methylene)benzamide exhibiting an X-ray powder diffraction pattern comprising peaks at the following diffraction angles (2θ): 6.3±0.2, 7.3±0.2, 11.0±0.2, 12.8±0.2, 16.9±0.2, 19.2±0.2, 20.6±0.2, 22.2±0.2, 25.7±0.2, 26.0±0.2, and 35.7±0.2. In certain embodiments, the relative intensity of the peak at said diffraction angles (2θ) is at least 15%. In certain other embodiments, the relative intensity of the peak at said diffraction angles (2θ) is at least 18%.

In certain embodiments, crystalline Form II may be further characterized as comprising the following (expressed in terms of diffraction angle 2θ, inter-planar distances d, and relative intensity (expressed as a percentage with respect to the most intense peak)) features in an X-ray powder diffraction pattern:

| Angle [2θ] | d-spacing [Å] | Relative Intensity [%] |
|---|---|---|
| 6.33 | 13.95 | 65.8 |
| 7.32 | 12.06 | 100.0 |
| 9.73 | 9.08 | 14.8 |
| 11.03 | 8.01 | 55.9 |
| 12.76 | 6.93 | 18.3 |
| 16.07 | 5.51 | 12.7 |
| 16.91 | 5.24 | 27.2 |
| 19.18 | 4.62 | 42.0 |
| 20.56 | 4.31 | 19.8 |
| 22.20 | 4.00 | 88.4 |
| 22.51 | 3.95 | 43.5 |
| 23.11 | 3.85 | 56.1 |
| 23.55 | 3.77 | 29.0 |
| 25.65 | 3.47 | 48.8 |
| 25.96 | 3.43 | 100.0 |
| 26.75 | 3.33 | 26.2 |
| 28.03 | 3.18 | 52.6 |
| 29.03 | 3.07 | 44.7 |
| 29.51 | 3.02 | 29.3 |
| 30.45 | 2.93 | 20.0 |
| 31.82 | 2.81 | 20.4 |
| 32.27 | 2.77 | 29.9 |
| 35.66 | 2.52 | 59.6 |

Crystalline Form II may be further characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
|---|---|---|
| 6.33 | 13.95 | 65.8 |
| 7.32 | 12.06 | 100.0 |
| 9.73 | 9.08 | 14.8 |
| 11.03 | 8.01 | 55.9 |
| 12.76 | 6.93 | 18.3 |
| 13.27 | 6.67 | 9.7 |
| 14.75 | 6.00 | 9.3 |
| 16.07 | 5.51 | 12.7 |
| 16.91 | 5.24 | 27.2 |
| 18.45 | 4.80 | 9.9 |
| 19.18 | 4.62 | 42.0 |
| 19.53 | 4.54 | 8.3 |
| 20.56 | 4.31 | 19.8 |
| 22.20 | 4.00 | 88.4 |
| 22.51 | 3.95 | 43.5 |
| 23.11 | 3.85 | 56.1 |
| 23.55 | 3.77 | 29.0 |
| 25.65 | 3.47 | 48.8 |
| 25.96 | 3.43 | 100.0 |
| 26.75 | 3.33 | 26.2 |
| 28.03 | 3.18 | 52.6 |
| 29.03 | 3.07 | 44.7 |
| 29.51 | 3.02 | 29.3 |
| 30.45 | 2.93 | 20.0 |
| 31.49 | 2.84 | 17.8 |
| 31.82 | 2.81 | 20.4 |
| 32.27 | 2.77 | 29.9 |
| 33.15 | 2.70 | 16.8 |
| 34.18 | 2.62 | 12.9 |
| 35.66 | 2.52 | 59.6 |
| 36.03 | 2.49 | 17.7 |
| 36.84 | 2.44 | 13.5 |
| 37.75 | 2.38 | 14.8 |
| 38.27 | 2.35 | 10.9 |
| 38.99 | 2.31 | 13.6 |
| 39.71 | 2.27 | 13.5 |
| 42.15 | 2.14 | 11.2 |
| 43.46 | 2.08 | 13.7 |

-continued

| Angle [2θ] | d-spacing [Å] | Relative Intensity [%] |
|---|---|---|
| 44.19 | 2.05 | 8.3 |
| 44.55 | 2.03 | 13.1 |
| 45.96 | 1.97 | 16.3 |
| 46.46 | 1.95 | 16.6 |
| 48.33 | 1.88 | 9.4 |
| 49.33 | 1.85 | 9.9 |
| 50.27 | 1.81 | 9.3 |
| 50.48 | 1.81 | 9.9 |
| 51.25 | 1.78 | 8.2 |
| 51.45 | 1.77 | 9.5 |
| 53.86 | 1.70 | 9.1 |
| 55.63 | 1.65 | 9.8 |
| 56.54 | 1.63 | 6.5 |
| 57.53 | 1.60 | 8.8 |
| 59.28 | 1.56 | 6.4 |

Figure 5:
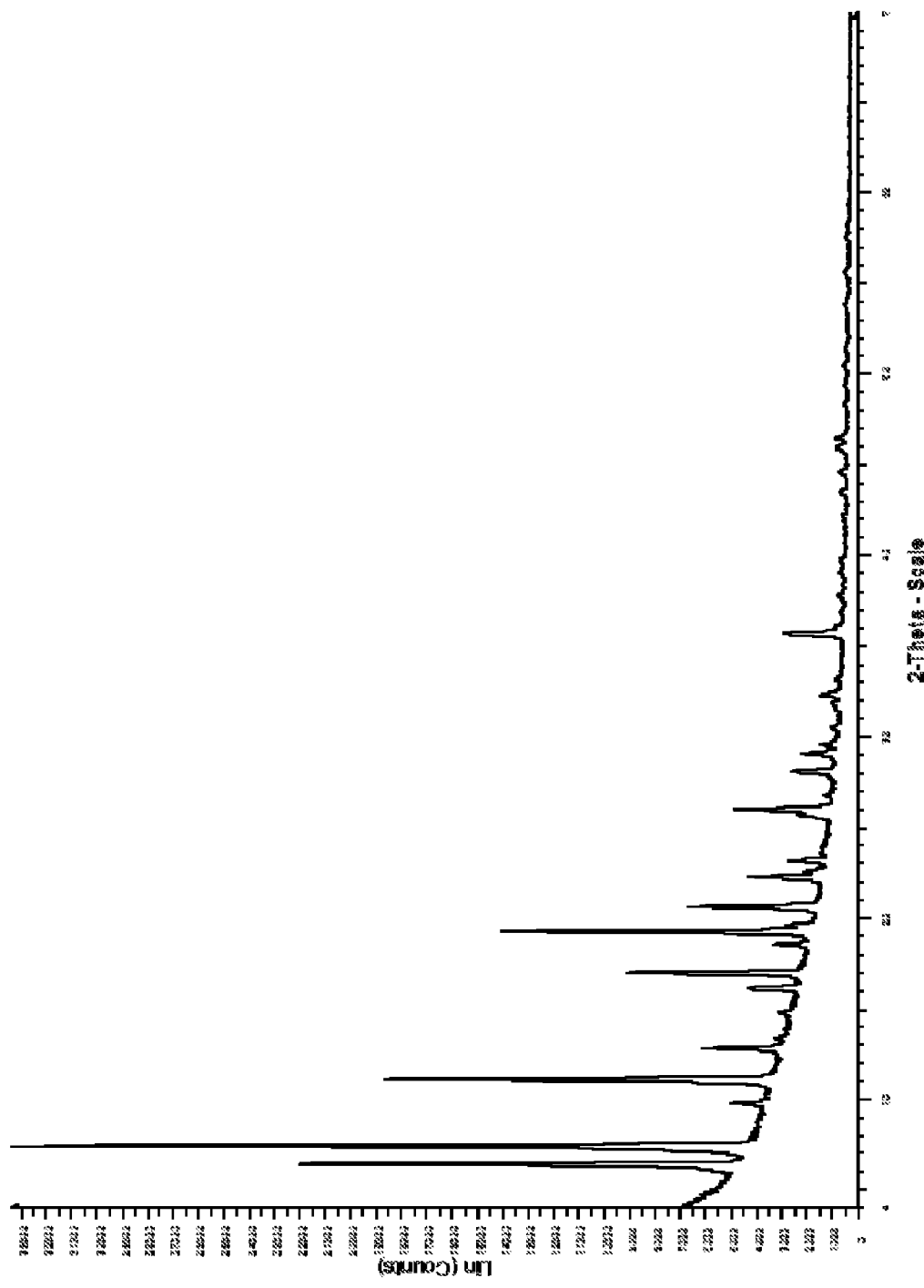
FIG. 5 is an X-ray powder diffractogram of crystalline Form II of 3-chloro-N-(((3-chloro-5-fluorophenyl)amino)((5-(trifluoromethyl)-1H-pyrazol-3-yl)amino)methylene)benzamide, as further described in Example 4.
Figure 7:
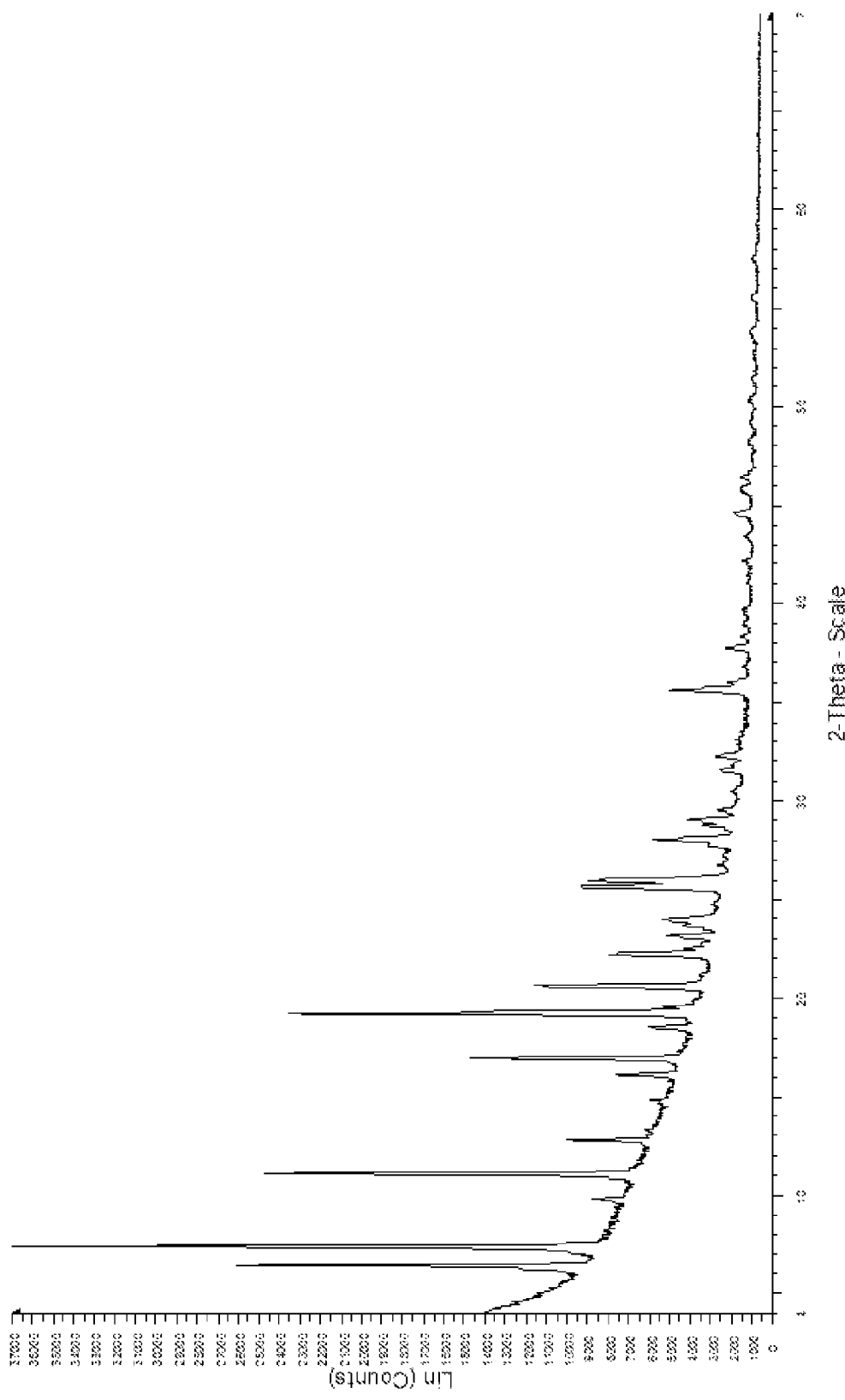
FIG. 7 is an X-ray powder diffractogram of crystalline Form II of 3-chloro-N-(((3-chloro-5-fluorophenyl)amino)((5-(trifluoromethyl)-1H-pyrazol-3-yl)amino)methylene)benzamide, as further described in Example 5.

In still further embodiments, crystalline Form II may be further characterized as having an X-ray powder diffraction pattern substantially as shown in FIG. 5. In other embodiments, crystalline Form II may be further characterized as having a X-ray powder diffraction pattern substantially as shown in FIG. 7.

An X-ray powder diffraction pattern may be obtained using CuKα radiation. The temperature at which the X-ray powder diffraction pattern is obtained may be, for example, 25±2 degrees Celsius.

Figure 6:
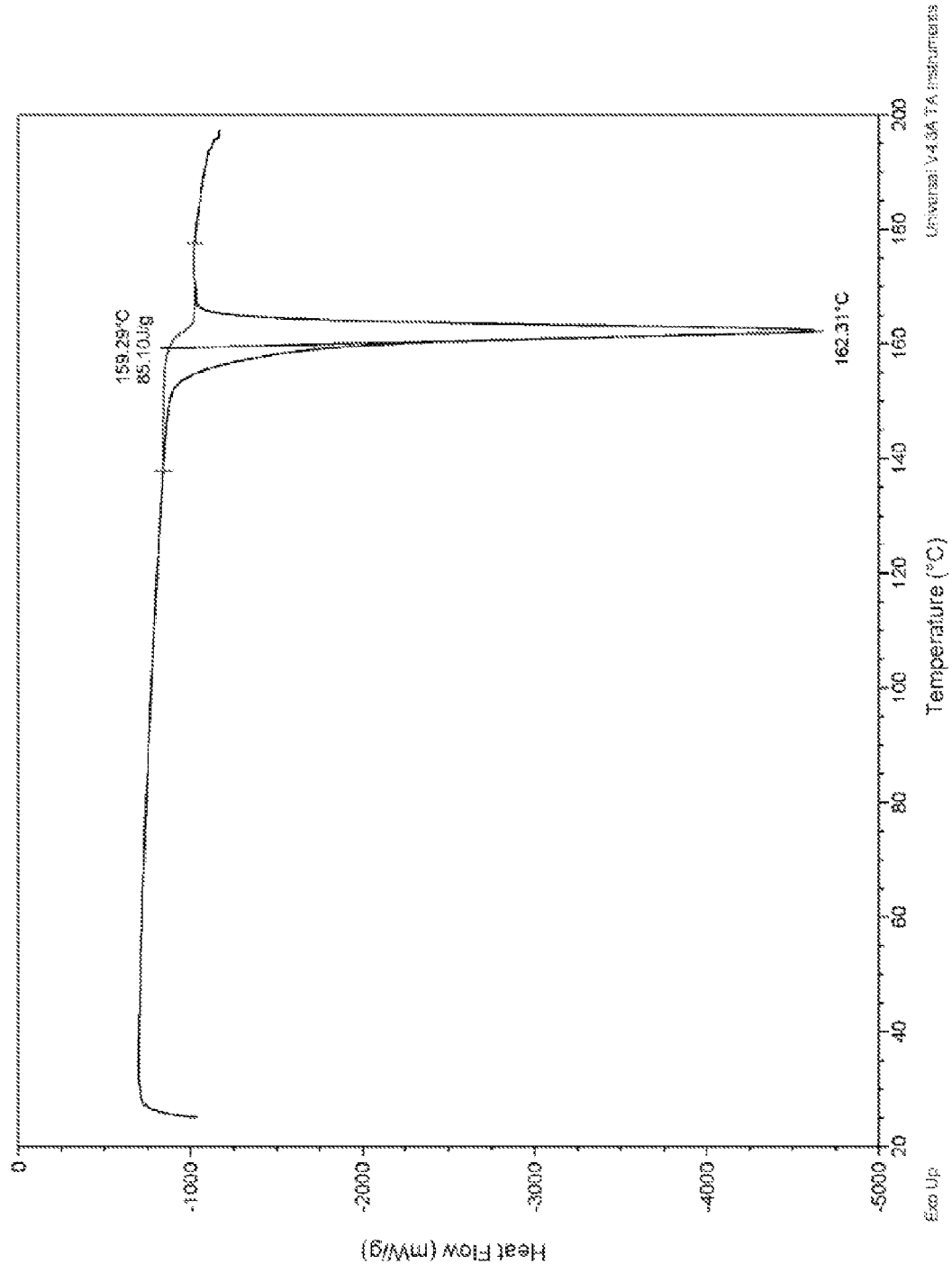
FIG. 6 is a differential scanning calorimetry (DSC) curve of crystalline Form II of 3-chloro-N-(((3-chloro-5-fluorophenyl)amino)((5-(trifluoromethyl)-1H-pyrazol-3-yl)amino)methylene)benzamide, as further described in Example 4.
Figure 8:
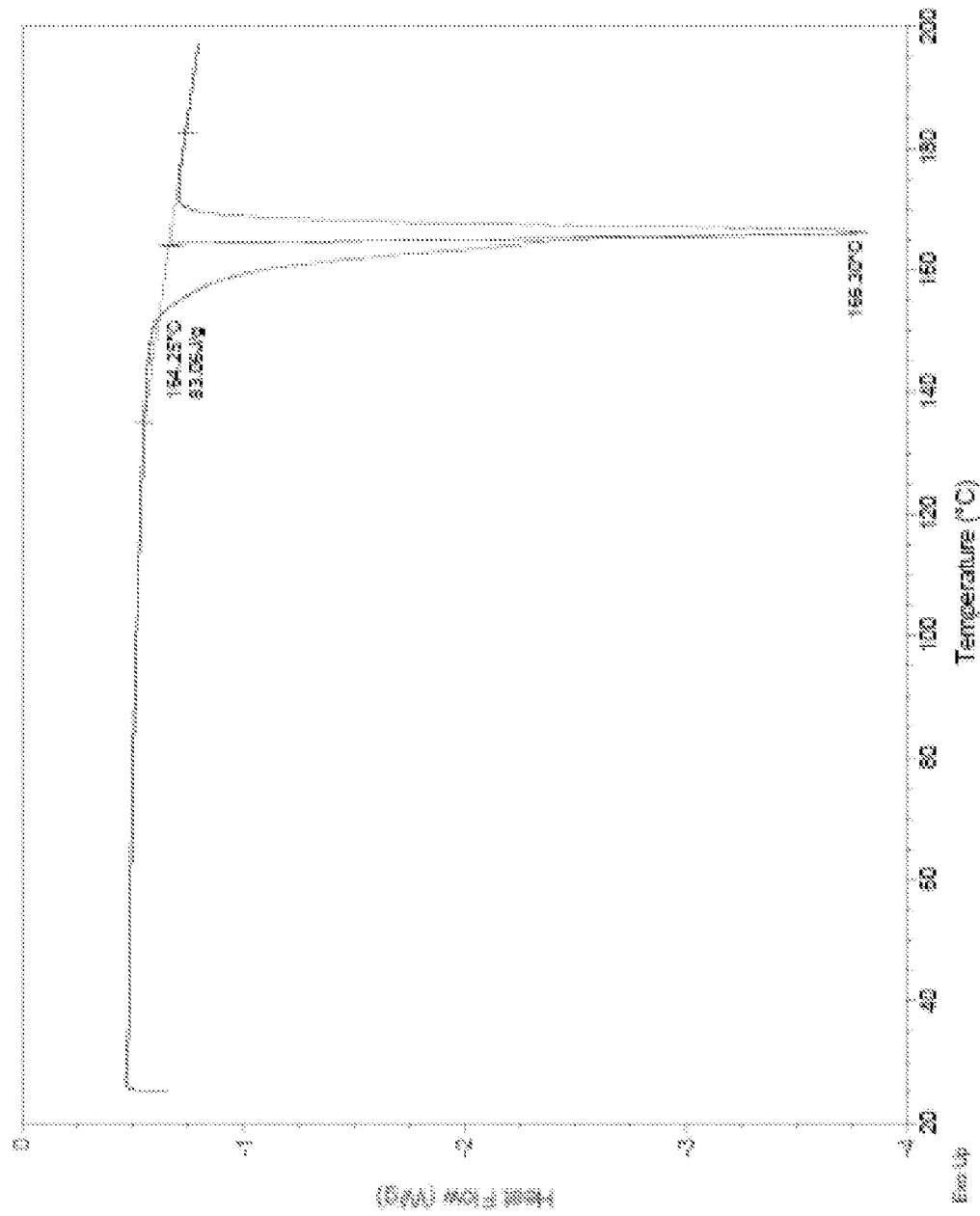
FIG. 8 is a differential scanning calorimetry curve of crystalline Form II of 3-chloro-N-(((3-chloro-5-fluorophenyl)amino)((5-(trifluoromethyl)-1H-pyrazol-3-yl)amino)methylene)benzamide, as further described in Example 5.

Crystalline Form II may be further characterized by its temperature of melting point onset as determined by differential scanning calorimetry. In certain embodiments, the crystalline compound has a melting point onset as determined by differential scanning calorimetry in the range of from about 158 degrees Celsius to about 165 degrees Celsius. In certain other embodiments, the crystalline compound has a melting point onset as determined by differential scanning calorimetry in the range of from about 159 degrees Celsius to about 164 degrees Celsius. In yet other embodiments, the crystalline compound has a melting point onset as determined by differential scanning calorimetry at about 158 degrees Celsius, about 159 degrees Celsius, about 160 degrees Celsius, about 163 degrees Celsius, about 164 degrees Celsius, or about 165 degrees Celsius. In yet other embodiments, the crystalline compound has a melting point onset as determined by differential scanning calorimetry at about 159 degrees Celsius. Further yet, crystalline Form II may be further characterized by having a differential scanning calorimetry curve substantially the same as shown in FIG. 6. In yet other embodiments, crystalline Form II may be further characterized by having a differential scanning calorimetry curve substantially the same as shown in FIG. 8.

C. Crystalline 3-Chloro-N-(((3-chloro-5-fluorophenyl)amino)((5-(trifluoromethyl)-1H-pyrazol-3-yl)amino)methylene)benzamide Acetone Solvate Procedures for making crystalline 3-chloro-N-(((3-chloro-5-fluorophenyl)amino)((5-(trifluoromethyl)-1H-pyrazol-3-yl)amino)methylene)benzamide acetone solvate are described in, for instance, Example 2 herein. An X-ray powder diffractogram of crystalline 3-chloro-N-(((3-chloro-5-fluorophenyl)amino)((5-(trifluoromethyl)-1H-pyrazol-3-yl)amino)methylene)benzamide acetone solvate is provided in FIG. 1. A differential scanning calorimetry curve of is provided in FIG. 2, along with a thermal gravimetric analysis curve. 3-Chloro-N-(((3-chloro-5-fluorophenyl)amino)((5-(trifluoromethyl)-1H-pyrazol-3-yl)amino)methylene)benzamide acetone solvate can be characterized according its X-ray powder diffractogram and its melting point onset as determined by differential scanning calorimetry.

Accordingly, one aspect of the invention provides a crystalline 3-chloro-N-(((3-chloro-5-fluorophenyl)amino)((5-(trifluoromethyl)-1H-pyrazol-3-yl)amino)methylene)benzamide acetone solvate exhibiting an X-ray powder diffraction pattern comprising peaks at the following diffraction angles (2θ): 6.2±0.2, 8.3±0.2, 14.7±0.2, 17.5±0.2, 17.9±0.2, 18.5±0.2, 20.2±0.2, 20.9±0.2, 23.5±0.2, and 25.9±0.2. In certain embodiments, wherein the relative intensity in said diffraction angles (2θ) is at least 10%. In certain other embodiments, wherein the relative intensity in said diffraction angles (2θ) is at least 15%.

The crystalline compound may be further characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
|---|---|---|
| 6.2 | 14.3 | 100 |
| 7.2 | 12.3 | 14.4 |
| 8.3 | 10.7 | 54.6 |
| 14.7 | 6.0 | 32.6 |
| 15.7 | 5.6 | 12.6 |
| 15.8 | 5.6 | 16.2 |
| 16.8 | 5.3 | 13.5 |
| 17.5 | 5.1 | 39.7 |
| 17.9 | 5.0 | 20.7 |
| 18.5 | 4.8 | 23.3 |
| 19.0 | 4.7 | 23.0 |
| 19.6 | 4.5 | 11.4 |
| 20.1 | 4.4 | 18.1 |
| 20.2 | 4.4 | 23.5 |
| 20.4 | 4.3 | 10.8 |
| 20.9 | 4.3 | 31.0 |
| 21.9 | 4.1 | 11.9 |
| 23.5 | 3.8 | 20.2 |
| 23.7 | 3.7 | 13.4 |
| 24.1 | 3.7 | 12.2 |
| 24.4 | 3.7 | 21.0 |
| 24.6 | 3.6 | 16.0 |
| 25.3 | 3.5 | 13.4 |
| 25.9 | 3.4 | 60.9 |
| 26.5 | 3.4 | 12.9 |
| 27.9 | 3.2 | 10.9 |
| 28.1 | 3.2 | 11.9 |
| 29.1 | 3.1 | 14.0 |

In still further embodiments, crystalline 3-chloro-N-(((3-chloro-5-fluorophenyl)amino)((5-(trifluoromethyl)-1H-pyrazol-3-yl)amino)methylene)benzamide acetone solvate may be further characterized as having a X-ray powder diffraction pattern substantially as shown in FIG. 1.

An X-ray powder diffraction pattern may be obtained using CuKα radiation. The temperature at which the X-ray powder diffraction pattern is obtained may be, for example, 25±2 degrees Celsius.

Figure 2:
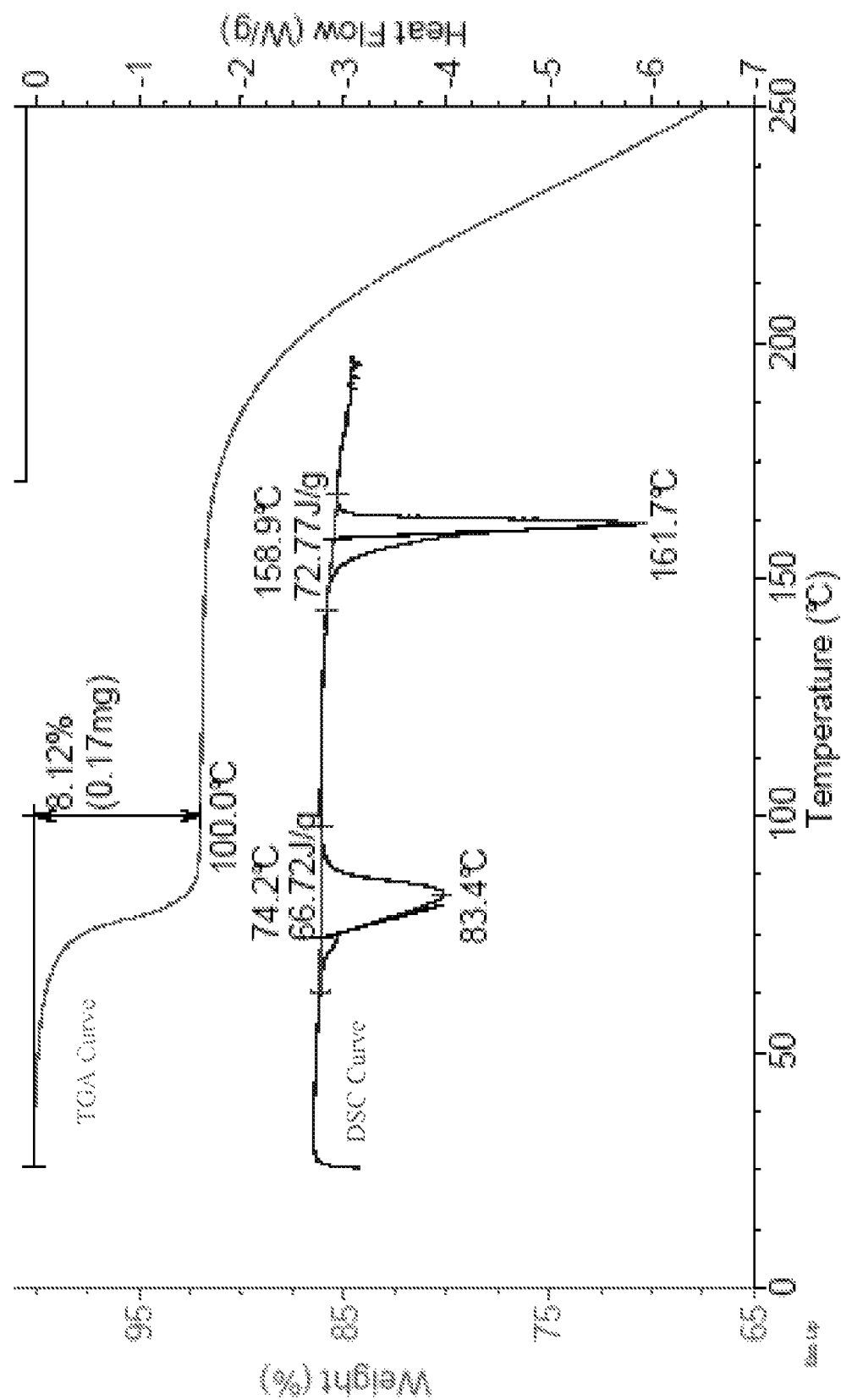
FIG. 2 is a differential scanning calorimetry (DSC) curve of 3-chloro-N-(((3-chloro-5-fluorophenyl)amino)((5-(trifluoromethyl)-1H-pyrazol-3-yl)amino)methylene)benzamide acetone solvate, along with a thermal gravimetric analysis (TGA) curve of 3-chloro-N-(((3-chloro-5-fluorophenyl) amino)((5-(trifluoromethyl)-1H-pyrazol-3-yl)amino) methylene)benzamide acetone solvate, each as further described in Example 2.

Crystalline 3-chloro-N-(((3-chloro-5-fluorophenyl)amino)((5-(trifluoromethyl)-1H-pyrazol-3-yl)amino)methylene)benzamide acetone solvate may be further characterized by having a melting point onset at about 159 degrees Celsius. Further yet, the crystalline compound may be further characterized by a differential scanning calorimetry curve substantially the same as shown in FIG. 2.

In certain other embodiments, the compound is one of the compounds listed in Examples 1-7, or a pharmaceutically acceptable salt of said compounds. In certain other embodiments, the compound is one of the compounds listed in Examples 1-8, or a pharmaceutically acceptable salt of said compounds. It is understood that the foregoing compounds can be combined with a pharmaceutically acceptable carrier to produce a pharmaceutical composition.

Exemplary methods for preparing compounds described herein are provided in the examples.

III. Therapeutic Applications of Trifluoromethyl Pyrazolyl Guanidine Compounds

It is contemplated that the guanidine compounds described herein, such as the guanidine compounds of Formula I and specific crystalline compounds described herein, provide therapeutic benefits to patients suffering from any one or more of a number of conditions, e.g., diseases characterized by dysregulation of $F_1F_0$-ATPase activity, diseases characterized by dysregulation of necrosis and/or apoptosis processes in a cell or tissue, and diseases characterized by aberrant cell growth and/or hyperproliferation. The compounds described herein can also be used to treat a variety of dysregulatory disorders related to cellular death as described elsewhere herein. Additionally, the compounds described herein can be used to inhibit ATP synthesis.

Accordingly, one aspect of the invention provides a method of treating a subject suffering from a medical disorder. The method comprises administering to the subject a therapeutically effective amount of one or more guanidine compounds described herein, e.g., a compound of Formula I or specific crystalline compound, as described in Section II above, in order to ameliorate a symptom of the disorder.

A large number of medical disorders can be treated using the guanidine compounds described herein. For example, the compounds described herein can be used to treat medical disorders characterized by dysregulation of necrosis and/or apoptosis processes in a cell or tissue, diseases characterized by aberrant cell growth and/or hyperproliferation, etc., or lupus, rheumatoid arthritis, psoriasis, graft-versus-host disease, Crohn's disease, inflammatory bowel disease, multiple sclerosis, cardiovascular disease, myeloma, lymphoma, cancer, and bacterial infection. In certain embodiments, the cancer is a solid tumor, leukemia, colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, small cell lung cancer, non-small cell lung cancer, bladder cancer, stomach cancer, cervical cancer, testicular tumor, skin cancer, rectal cancer, thyroid cancer, kidney cancer, uterus cancer, espophagus cancer, liver cancer, an acoustic neuroma, oligodendroglioma, meningioma, melanoma, neuroblastoma, or retinoblastoma.

Although not wishing to be bound to a particular theory, it is believed that the compounds impart therapeutic benefit by modulating (e.g., inhibiting or promoting) the activity of the $F_1F_0$-ATPase complexes (e.g., mitochondrial $F_1F_0$-ATPase complexes) in affected cells or tissues. In some embodiments, the compositions of the present invention are used to treat immune/chronic inflammatory conditions (e.g., psoriasis, autoimmune disorders, organ-transplant rejection, and epidermal hyperplasia). In further embodiments, the compositions of the present invention are used in conjunction with stenosis therapy to treat compromised (e.g., occluded) vessels.

In certain embodiments, a composition comprising a guanidine compound is administered under conditions (e.g., timing, dose, co-administration with other agent, mode of administration, selection of subject, use of targeting agents, etc.) that maximize desired effects directed at the $F_1F_0$-ATPase.

In certain embodiments, the medical disorder is an immune disorder. In certain other embodiments, the medical disorder is an inflammatory disorder. In certain other embodiments, the medical disorder is an autoimmune disorder. In certain other embodiments, the medical disorder is rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, uveitis, or epidermal hyperplasia.

In certain embodiments, the medical disorder is Crohn's disease or ulcerative colitis.

In certain other embodiments, the medical disorder is cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, or autoimmune hepatitis. In certain embodiments, the psoriasis is plaque psoriasis, guttate psoriasis, inverse psoriasis, pustular psoriasis, or erythrodermic psoriasis.

In certain other embodiments, the medical disorder is Crohn's disease, inflammatory bowel disease, multiple sclerosis, graft-versus-host disease, lupus, rheumatoid arthritis, or psoriasis. In certain other embodiments, the medical disorder is cardiovascular disease, myeloma, lymphoma, or cancer. In certain other embodiments, the medical disorder is lupus, rheumatoid arthritis, psoriasis, graft-versus-host disease, myeloma, or lymphoma. In certain other embodiments, the medical disorder is cardiovascular disease or cancer. In certain other embodiments, the medical disorder is Crohn's disease, inflammatory bowel disease, or multiple sclerosis. In certain other embodiments, the medical disorder is graft-versus-host disease. In further embodiments, the medical disorder is a bacterial infection. In certain embodiments, the patient (or subject) is a human.

As indicated above, the guanidine compounds described herein can be used in the treatment of a bacterial infection. A variety of bacteria are contemplated to be susceptible to the guanidine compounds. Representative bacteria include Staphylococci species, e.g., *S. aureus; Enterococci* species, e.g., *E. faecalis* and *E. faecium; Streptococci* species, e.g., *S. pyogenes* and *S. pneumoniae; Escherichia* species, e.g., *E. coli*, including enterotoxigenic, enteropathogenic, enteroinvasive, enterohemorrhagic and enteroaggregative *E. coli* strains; *Haemophilus* species, e.g., *H. influenza*; and *Moraxella* species, e.g., *M. catarrhalis*. Other examples include *Mycobacteria* species, e.g., *M. tuberculosis, M. avian-intracellulare, M. kansasii, M bovis, M. africanum, M. genavense, M. leprae, M. xenopi, M simiae, M. scrofulaceum, M. malmoense, M celatum, M abscessus, M. chelonae, M. szulgai, M. gordonae, M. haemophilum, M. fortuni* and *M. marinum; Corynebacte-* ria species, e.g., *C. diphtheriae*; *Vibrio* species, e.g., *V. cholerae*; *Campylobacter* species, e.g., *C. jejuni*; *Helicobacter* species, e.g., *H. pylori*; *Pseudomonas* species, e.g., *P. aeruginosa*; *Legionella* species, e.g., *L. pneumophila*; *Treponema* species, e.g., *T. pallidum*; *Borrelia* species, e.g., *B. burgdorferi*; *Listeria* species, e.g., *L monocytogenes*; *Bacillus* species, e.g., *B. cereus*; *Bordatella* species, e.g., *B. pertussis*; *Clostridium* species, e.g., *C. perfringens, C. tetani, C. difficile* and *C. botulinum*; *Neisseria* species, e.g., *N. meningitidis* and *N. gonorrhoeae*; *Chlamydia* species, e.g., *C. psittaci, C. pneumoniae* and *C. trachomatis*; *Rickettsia* species, e.g., *R. rickettsii* and *R. prowazekii*; *Shigella* species, e.g., *S. sonnei*; *Salmonella* species, e.g., *S. typhimurium*; *Yersinia* species, e.g., *Y. enterocolitica* and *Y. pseudotuberculosis*; *Klebsiella* species, e.g., *K. pneumoniae*; *Mycoplasma* species, e.g., *M. pneumoniae*; and *Trypanosoma brucei*. In certain embodiments, the guanidine compounds described herein are used to treat a subject suffering from a bacterial infection selected from the group consisting of *S. aureus, E. faecalis, E. faecium, S. pyogenes, S. pneumonia*, and *P. aeruginosa*. In certain embodiments, the guanidine compounds described herein are used to treat a subject suffering from a *Trypanosoma brucei* infection.

The antibacterial activity of the compounds described herein may be evaluated using standard assays known in the art, such as the microbroth dilution minimum inhibition concentration (MIC) assay, as further described in National Committee for Clinical Laboratory Standards. Performance Standards for Antimicrobial Susceptibility Testing; Fourteenth Informational Supplement. NCCLS document M100-S14 {ISBN 1-56238-516-X}. This assay may be used to determine the minimum concentration of a compound necessary to prevent visible bacterial growth in a solution. In general, the drug to be tested is serially diluted into wells, and aliquots of liquid bacterial culture are added. This mixture is incubated under appropriate conditions, and then tested for growth of the bacteria. Compounds with low or no antibiotic activity (a high MIC) will allow growth at high concentrations of compound, while compounds with high antibiotic activity will allow bacterial growth only at lower concentrations (a low MIC).

The assay uses stock bacterial culture conditions appropriate for the chosen strain of bacteria. Stock cultures from the permanent stock culture collection can be stored as frozen suspensions at −70° C. Cultures may be suspended in 10% skim milk (BD) prior to snap freezing in dry ice/ethanol and then placed in a −70° C. freezer. Cultures may be maintained on Tryptic Soy Agar containing 5% Sheep Blood at room temperature (20° C.), and each culture may be recovered from frozen form and transferred an additional time before MIC testing. Fresh plates are inoculated the day before testing, incubated overnight, and checked to confirm purity and identity.

The identity and purity of the cultures recovered from the stock culture can be confirmed to rule out the possibility of contamination. The identity of the strains may be confirmed by standard microbiological methods (See, e.g., Murray et al., Manual of Clinical Microbiology, Eighth Edition. ASM Press {ISBN 1-55581-255-4}). In general, cultures are streaked onto appropriate agar plates for visualization of purity, expected colony morphology, and hemolytic patterns. Gram stains can also be utilized. The identities are confirmed using a MicroScan WalkAway 40 SI Instrument (Dade Behring, West Sacramento, Calif.). This device utilizes an automated incubator, reader, and computer to assess for identification purposes the biochemical reactions carried out by each organism. The MicroScan WalkAway can also be used to determine a preliminary MIC, which may be confirmed using the method described below.

Frozen stock cultures may be used as the initial source of organisms for performing microbroth dilution minimum inhibition concentration (MIC) testing. Stock cultures are passed on their standard growth medium for at least 1 growth cycle (18-24 hours) prior to their use. Most bacteria may be prepared directly from agar plates in 10 mL aliquots of the appropriate broth medium. Bacterial cultures are adjusted to the opacity of a 0.5 McFarland Standard (optical density value of 0.28-0.33 on a Perkin-Elmer Lambda EZ150 Spectrophotometer, Wellesley, Mass., set at a wavelength of 600 nm). The adjusted cultures are then diluted 400 fold (0.25 mL inoculum+100 mL broth) in growth media to produce a starting suspension of approximately 5×105 colony forming units (CFU)/mL. Most bacterial strains may be tested in cation adjusted Mueller Hinton Broth (CAMHB).

Test compounds ("drugs") are solubilized in a solvent suitable for the assay, such as DMSO. Drug stock solutions may be prepared on the day of testing. Microbroth dilution stock plates may be prepared in two dilution series, 64 to 0.06 µg drug/mL and 0.25 to 0.00025 µg drug/mL. For the high concentration series, 200 µL of stock solution (2 mg/mL) is added to duplicate rows of a 96-well microtiter plate. This is used as the first well in the dilution series. Serial two-fold decremental dilutions are made using a BioMek FX robot (Beckman Coulter Inc., Fullerton, Calif.) with 10 of the remaining 11 wells, each of which will contain 100 µL of the appropriate solvent/diluent. Row 12 contains solvent/diluent only and serves as the control. For the first well of the low concentration series, 200 µL of an 8 µg/mL stock are added to duplicate rows of a 96-well plate. Serial two-fold dilutions are made as described above.

Daughter 96-well plates may be spotted (3.2 µL/well) from the stock plates listed above using the BioMek FX robot and used immediately or frozen at −70° C. until use. Aerobic organisms are inoculated (100 µL volumes) into the thawed plates using the BioMek FX robot. The inoculated plates are be placed in stacks and covered with an empty plate. These plates are then incubated for 16 to 24 hours in ambient atmosphere according to CLSI guidelines (National Committee for Clinical Laboratory Standards, Methods for Dilution, Antimicrobial Tests for Bacteria that Grow Aerobically; Approved Standard-Sixth Edition. NCCLS document M7-A6 {ISBN 1-56238-486-4}).

After inoculation and incubation, the degree of bacterial growth can be estimated visually with the aid of a Test Reading Mirror (Dynex Technologies 220 16) in a darkened room with a single light shining directly through the top of the microbroth tray. The MIC is the lowest concentration of drug that prevents macroscopically visible growth under the conditions of the test.

Additionally, any one or more of the pyrazolyl guanidine compounds described herein can be used to treat a $F_1F_0$-ATP hydrolase associated disorder (e.g., myocardial infarction, ventricular hypertrophy, coronary artery disease, non-Q wave MI, congestive heart failure, cardiac arrhythmias, unstable angina, chronic stable angina, Prinzmetal's angina, high blood pressure, intermittent claudication, peripheral occlusive arterial disease, thrombotic or thromboembolic symptoms of thromboembolic stroke, venous thrombosis, arterial thrombosis, cerebral thrombosis, pulmonary embolism, cerebral embolism, thrombophilia, disseminated intravascular coagulation, restenosis, atrial fibrillation, ventricular enlargement, atherosclerotic vascular disease, atherosclerotic plaque rupture, atherosclerotic plaque formation, transplant atherosclerosis, vascular remodeling atherosclerosis, cancer, surgery, inflammation, systematic infection, artificial surfaces, interventional cardiology, immobility, medication, pregnancy and fetal loss, and diabetic complications comprising retinopathy, nephropathy and neuropathy) in a subject.

Combination Therapy

Additionally, the guanidine compounds described herein can be used in combination with at least one other therapeutic agent, such as Bz-423 (a benzodiazepine compound as described in U.S. Pat. Nos. 7,144,880 and 7,125,866, U.S. patent application Ser. Nos. 11/586,097, 11/585,492, 11/445,010, 11/324,419, 11/176,719, 11/110,228, 10/935,333, 10/886,450, 10/795,535, 10/634,114, 10/427,211, 10/217,878, and 09/767,283, and U.S. Provisional Patent Nos. 60/878,519, 60/812,270, 60/802,394, 60/732,045, 60/730,711, 60/704,102, 60/686,348, 60/641,040, 60/607,599, and 60/565,788), potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents selected from ACE inhibitors, AT-1 receptor antagonists, ET receptor antagonists, dual ET/AII receptor antagonists, vasopepsidase inhibitors, an antiplatelet agent selected from GPIIb/IIIa blockers, $P2Y_1$ and $P2Y_{12}$ antagonists, thromboxane receptor antagonists, or aspirin, along with a pharmaceutically-acceptable carrier or diluent in a pharmaceutical composition.

IV. Pharmaceutical Compositions, Formulations, and Exemplary Administration Routes and Dosing Considerations Exemplary embodiments of various contemplated medicaments and pharmaceutical compositions are provided below.

A. Preparing Medicaments

Compounds of the present invention are useful in the preparation of medicaments to treat a variety of conditions, such as conditions associated with dysregulation of cell death, aberrant cell growth and hyperproliferation. One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as discussed above, together with a solid support or alternatively, together with one or more pharmaceutically acceptable carriers and optionally other therapeutic agents (e.g., those described in section III hereinabove). Each carrier should be "acceptable" in the sense that it is compatible with the other ingredients of the formulation and not injurious to the subject.

Contemplated formulations include those suitable for oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets and capsules may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprise a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, and include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer therapeutic agents (e.g., exemplary compounds as described above) of the present invention, e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified can be administered to subjects or individuals susceptible to or at risk of developing pathological growth of target cells and correlated conditions. When the agent is administered to a subject such as a mouse, a rat or a human patient, the agent can be added to a pharmaceutically acceptable carrier and systemically or topically administered to the subject. To identify patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent. One example of an animal model is MLR/MpJ-lpr/lpr ("MLR-lpr") (available from Jackson Laboratories, Bar Harbor, Me.). MLR-lpr mice develop systemic autoimmune disease. Alternatively, other animal models can be developed by inducing tumor growth, for example, by subcutaneously inoculating nude mice with about $10^5$ to about $10^9$ hyperproliferative, cancer or target cells as defined herein. When the tumor is established, the compounds described herein are administered, for example, by subcutaneous injection around the tumor. Tumor measurements to determine reduction of tumor size are made in two dimensions using venier calipers twice a week. Other animal models may also be employed as appropriate. Such animal models for the above-described diseases and conditions are well-known in the art.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or non-aqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or by oral administration, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component than may be required when each individual therapeutic compound or drug is used alone, thereby reducing adverse effects.

D. Exemplary Co-Administration Routes and Dosing Considerations

The invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depend on the type of condition being treated. For example, when the condition being treated is cancer, the additional agent can be a chemotherapeutic agent or radiation. When the condition being treated is an immune disorder, the additional agent can be an immunosuppressant or an anti-inflammatory agent. When the condition being treated is chronic inflammation, the additional agent can be an anti-inflammatory agent. The additional agents to be co-administered, such as anticancer, immunosuppressant, anti-inflammatory, can be any of the well-known agents in the art, including, but not limited to, those that are currently in clinical use. The determination of appropriate type and dosage of radiation treatment is also within the skill in the art or can be determined with relative ease.

Treatment of the various conditions associated with abnormal apoptosis is generally limited by the following two major factors: (1) the development of drug resistance and (2) the toxicity of known therapeutic agents. In certain cancers, for example, resistance to chemicals and radiation therapy has been shown to be associated with inhibition of apoptosis. Some therapeutic agents have deleterious side effects, including non-specific lymphotoxicity, renal and bone marrow toxicity.

The methods described herein address both these problems. Drug resistance, where increasing dosages are required to achieve therapeutic benefit, is overcome by co-administering the compounds described herein with the known agent. The compounds described herein sensitize target cells to known agents (and vice versa) and, accordingly, less of these agents are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases where drug resistance has increased the requisite dosage. When the claimed compounds are co-administered with the known agent, they reduce the dosage required which, in turn, reduces the deleterious effects.

EXAMPLES

The invention now being generally described, will be more readily understood by reference to the following examples, which are included merely for purposes of illustration of certain aspects and embodiments of the present invention, and are not intended to limit the invention. Unless indicated otherwise, the HPLC method used is as follows: Waters Symmetry C-18 column, 4.6×150 mm, 3.5 micron, 25° C., 1.0 mL/min, 25 minute gradient of 5% MeCN in $H_2O$ (0.1% TFA) to 95% MeCN in $H_2O$ (0.1% TFA), then 95% MeCN in $H_2O$ (0.1% TFA) for 10 minutes, and then equilibration to 5% MeCN in $H_2O$ (0.1% TFA) over 5.0 minutes. The phrase "$H_2O$ (0.1% TFA)" is art-recognized and refers to water containing 0.1% v/v trifluoroacetic acid.

Example 1

Preparation of 3-Chloro-N-((3-Chloro-5-Fluorophenyl)Carbamothioyl)Benzamide

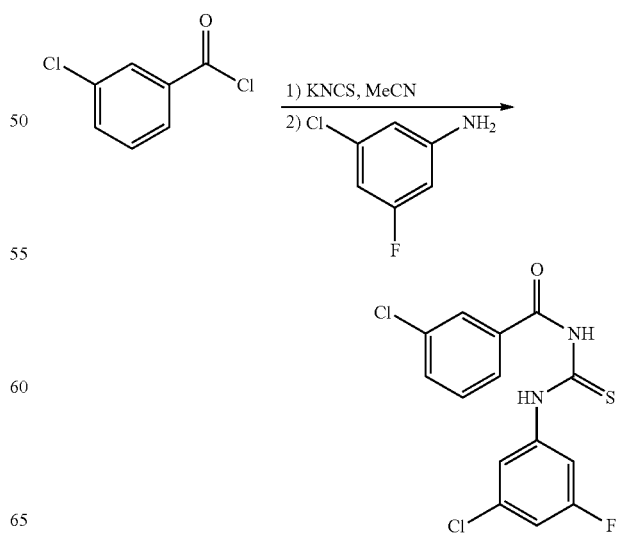

3-Chlorobenzoyl chloride (200 g, 1.14 mol) was dissolved in acetonitrile (4.5 L) and the reaction vessel containing this mixture was cooled in an ice/water bath. Potassium thiocyanate (122 g, 1.26 mol, 1.10 equiv) was added to the reaction mixture. The cooling bath was removed from the reaction vessel after 15 minutes and the resulting slurry was stirred at room temperature for approximately 1 hour. Next, 3-chloro-5-fluoroaniline (138 mL, 1.37 mol, 1.2 equiv) was added as a solution in acetonitrile (138 mL) over 5 minutes. The reaction mixture was then stirred at room temperature overnight and subsequently quenched with water (4.30 L), and then stirred at room temperature for 1 hour. The resulting solid was collected by filtration and rinsed with acetonitrile/water (1/1 mixture by volume, 780 mL). The solid was dried at 60° C. in vacuo to provide 390 g (99% yield) of the title compound as a solid. $^1$H NMR (DMSO-$d_6$) δ 12.5 (s, 1H), 11.9 (s, 1H), 8.01 (t, 1H, J=1.8), 7.89 (d, 1H, J=7.8), 7.69 (m, 3H), 7.56 (t, 1H, J=7.8), 7.34 (dt, 1H, J=8.7, 1.8). HPLC: >99% purity at 23.73 min.

Example 2

Preparation of Crystalline 3-Chloro-N-(((3-Chloro-5-Fluorophenyl)Amino)((5-(Trifluoromethyl)-1H-Pyrazol-3-Yl)Amino)Methylene)Benzamide Acetone Solvate

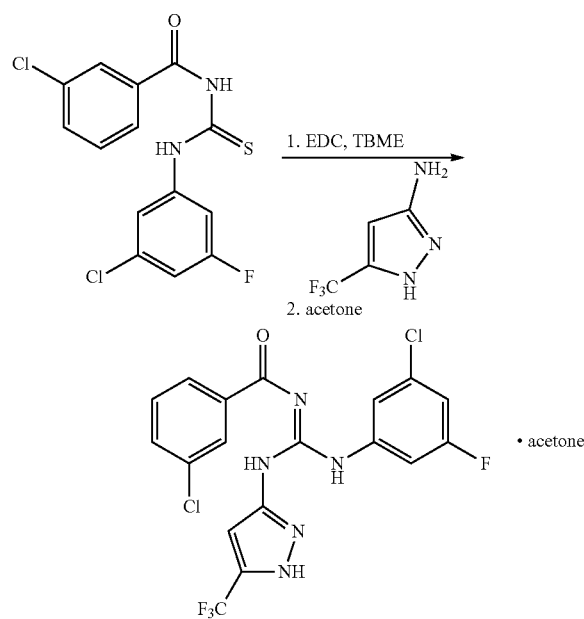

A suspension of 3-chloro-N-((3-chloro-5-fluorophenyl) carbamothioyl)benzamide (75 g, 219 mmol) in tert-butyl methyl ether (TBME) (1.1 L) was heated to 50° C. Next, 5-(trifluoromethyl)-1H-pyrazol-3-amine (39.6 g, 262 mmol, 1.20 equiv) and N-(3-dimethylaminopropyl)-N'-ethylcarbodiimide (EDC) (64.2 g, 328 mmol, 1.50 equiv) were added. The resulting reaction mixture was stirred at 50° C. for 1 hour and diluted with EtOAc (1.0 L) and water (1.0 L). The organic extract was washed with a saturated, aqueous sodium chloride solution (0.5 L), dried ($Na_2SO_4$), filtered, and concentrated. The resulting residue was diluted with EtOAc (300 mL) and this mixture was warmed to 50° C., then filtered through Celite. Next, the filtrate was concentrated to approximately 75 mL and slowly diluted with hexanes (750 mL). The resulting mixture was stirred at room temperature for 1 hour and filtered. The resulting solid was heated in acetone (100 mL), filtered, diluted with hexanes (100 mL), and the resulting mixture was heated until a clear solution developed. Next, the mixture was further diluted with hexanes (300 mL) and stirred at room temperature overnight. The resulting solids were collected by filtration, rinsed with hexanes (100 mL) and dried in vacuo at room temperature to afford (25.1 g, 25% yield) of crystalline 3-chloro-N-(((3-chloro-5-fluorophenyl) amino)((5-(trifluoromethyl)-1H-pyrazol-3-yl)amino)methylene)benzamide acetone solvate. $^1$H NMR analysis indicates that the molar ratio of 3-chloro-N-(((3-chloro-5-fluorophenyl)amino)((5-(trifluoromethyl)-1H-pyrazol-3-yl) amino)methylene)benzamide to acetone is 3 to 2. $^1$H NMR (DMSO-$d_6$) of the title compound: δ 13.3 (s, 1H), 10.7 (s, 1H), 10.0 (s, 1H), 7.90 (s, 1H), 7.82 (d, 1H, J=7.6), 7.69 (d, 1H, J=8.4), 7.58 (m, 2H), 7.07 (d, 1H, J=8.4), 6.03 (s, 1H), 2.05 (s, 4H, Acetone). HPLC: 97.6% purity at 26.08 min.

An X-ray powder diffractogram of the title composition is provided in FIG. 1. A differential scanning calorimetry curve of the title composition is provided in FIG. 2, along with a thermal gravimetric analysis curve. Tabulated characteristics of the X-ray powder diffractogram in FIG. 1 are provided below in Table 1, which lists diffraction angle 2θ, inter-planar distances d, and relative intensity (expressed as a percentage with respect to the most intense peak).

TABLE 1

X-RAY POWDER DIFFRACTOGRAM DATA.

| Angle [2θ] | d-spacing [Å] | Relative Intensity [%] |
|---|---|---|
| 6.2 | 14.3 | 100 |
| 7.2 | 12.3 | 14.4 |
| 8.3 | 10.7 | 54.6 |
| 14.7 | 6.0 | 32.6 |
| 15.7 | 5.6 | 12.6 |
| 15.8 | 5.6 | 16.2 |
| 16.8 | 5.3 | 13.5 |
| 17.5 | 5.1 | 39.7 |
| 17.9 | 5.0 | 20.7 |
| 18.5 | 4.8 | 23.3 |
| 19.0 | 4.7 | 23.0 |
| 19.6 | 4.5 | 11.4 |
| 20.1 | 4.4 | 18.1 |
| 20.2 | 4.4 | 23.5 |
| 20.4 | 4.3 | 10.8 |
| 20.9 | 4.3 | 31.0 |
| 21.9 | 4.1 | 11.9 |
| 23.5 | 3.8 | 20.2 |
| 23.7 | 3.7 | 13.4 |
| 24.1 | 3.7 | 12.2 |
| 24.4 | 3.7 | 21.0 |
| 24.6 | 3.6 | 16.0 |
| 25.3 | 3.5 | 13.4 |
| 25.9 | 3.4 | 60.9 |
| 26.5 | 3.4 | 12.9 |
| 27.9 | 3.2 | 10.9 |
| 28.1 | 3.2 | 11.9 |
| 29.1 | 3.1 | 14.0 |

Example 3

Preparation of Crystalline Form I of 3-Chloro-N-(((3-Chloro-5-Fluorophenyl)Amino)((5-(Trifluoromethyl)-1H-Pyrazol-3-Yl)Amino)Methylene)Benzamide 3-Chloro-N-(((3-chloro-5-fluorophenyl)amino)((5-(trifluoromethyl)-1H-pyrazol-3-yl)amino)methylene)benzamide, acetone solvate (16 g) was dried (60° C./10 Torr) to afford 3-chloro-N-(((3-chloro-5-fluorophenyl)amino)((5-(trifluoromethyl)-1H-pyrazol-3-yl)amino)methylene)benzamide as a crystalline solid designated herein as Form I. Analytical analysis did not identify solvate molecules in the crystalline solid. $^1$H NMR (DMSO-$d_6$) of the title compound: δ 13.3 (s, 1H), 10.7 (s, 1H), 10.0 (s, 1H), 7.90 (s, 1H), 7.82 (d, 1H, J=7.6), 7.69 (d, 1H, J=8.4), 7.58 (m, 2H), 7.07 (d, 1H, J=8.4), 6.03 (s, 1H). HPLC: 97.6% purity at 26.08 min.

An X-ray powder diffractogram of the title composition is provided in FIG. 3. A differential scanning calorimetry curve of the title composition is provided in FIG. 4, along with a thermal gravimetric analysis curve. Tabulated characteristics of the X-ray powder diffractogram in FIG. 3 are provided below in Table 2, which lists diffraction angle 2θ, inter-planar distances d, and relative intensity (expressed as a percentage with respect to the most intense peak).

TABLE 2

X-RAY POWDER DIFFRACTOGRAM DATA.

| Angle [2θ] | d-spacing [Å] | Relative Intensity [%] |
|---|---|---|
| 6.2 | 14.3 | 53.8 |
| 7.1 | 12.4 | 69.6 |
| 9.4 | 9.4 | 53.8 |
| 10.7 | 8.3 | 51.0 |
| 12.9 | 6.9 | 34.6 |
| 15.6 | 5.7 | 92.8 |
| 16.4 | 5.4 | 29.1 |
| 17.9 | 4.9 | 44.0 |
| 19.0 | 4.7 | 100.0 |
| 20.0 | 4.4 | 62.6 |
| 21.9 | 4.1 | 38.9 |
| 23.6 | 3.8 | 51.4 |
| 25.2 | 3.5 | 57.8 |
| 27.3 | 3.3 | 24.0 |
| 28.4 | 3.1 | 15.8 |
| 35.0 | 2.6 | 10.0 |

Example 4

Preparation of Crystalline Form II of 3-Chloro-N-(((3-Chloro-5-Fluorophenyl)Amino)((5-(Trifluoromethyl)-1H-Pyrazol-3-Yl)Amino)Methylene)Benzamide 3-Chloro-N-(((3-chloro-5-fluorophenyl)amino)((5-(trifluoromethyl)-1H-pyrazol-3-yl)amino)methylene)benzamide, acetone solvate (0.500 g) was dissolved in EtOH (5 mL) and warmed to 40° C. The mixture was clarified by filtration through celite and then diluted with EtOH/water (1/1 by volume, 1.25 mL) at 40° C. The suspension was further diluted with EtOH/water (1/1 by volume, 5 mL) at 40° C., and then the mixture was allowed to cool to room temperature and stirring was continued for 4 days. The resulting suspension was filtered, rinsed with EtOH/water (1/1 by volume, 5 mL), and dried (60° C./10 Torr) to afford 3-chloro-N-(((3-chloro-5-fluorophenyl)amino)((5-(trifluoromethyl)-1H-pyrazol-3-yl)amino)methylene)benzamide as a crystalline solid designated herein as Form II. Analytical analysis did not identify solvate molecules in the crystalline solid.

An X-ray powder diffractogram of the title composition is provided in FIG. 5. A differential scanning calorimetry curve of the title composition is provided in FIG. 6. Tabulated characteristics of the X-ray powder diffractogram in FIG. 5 are provided below in Table 3, which lists diffraction angle 2θ, inter-planar distances d, and relative intensity (expressed as a percentage with respect to the most intense peak).

TABLE 3

X-RAY POWDER DIFFRACTOGRAM DATA.

| Angle [2θ] | d-spacing [Å] | Relative Intensity [%] |
|---|---|---|
| 6.33 | 13.95 | 65.8 |
| 7.32 | 12.06 | 100.0 |
| 9.73 | 9.08 | 14.8 |
| 11.03 | 8.01 | 55.9 |
| 12.76 | 6.93 | 18.3 |
| 13.27 | 6.67 | 9.7 |
| 14.75 | 6.00 | 9.3 |
| 16.07 | 5.51 | 12.7 |
| 16.91 | 5.24 | 27.2 |
| 18.45 | 4.80 | 9.9 |
| 19.18 | 4.62 | 42.0 |
| 19.53 | 4.54 | 8.3 |
| 20.56 | 4.31 | 19.8 |
| 22.20 | 4.00 | 88.4 |
| 22.51 | 3.95 | 43.5 |
| 23.11 | 3.85 | 56.1 |
| 23.55 | 3.77 | 29.0 |
| 25.65 | 3.47 | 48.8 |
| 25.96 | 3.43 | 100.0 |
| 26.75 | 3.33 | 26.2 |
| 28.03 | 3.18 | 52.6 |
| 29.03 | 3.07 | 44.7 |
| 29.51 | 3.02 | 29.3 |
| 30.45 | 2.93 | 20.0 |
| 31.49 | 2.84 | 17.8 |
| 31.82 | 2.81 | 20.4 |
| 32.27 | 2.77 | 29.9 |
| 33.15 | 2.70 | 16.8 |
| 34.18 | 2.62 | 12.9 |
| 35.66 | 2.52 | 59.6 |
| 36.03 | 2.49 | 17.7 |
| 36.84 | 2.44 | 13.5 |
| 37.75 | 2.38 | 14.8 |
| 38.27 | 2.35 | 10.9 |
| 38.99 | 2.31 | 13.6 |
| 39.71 | 2.27 | 13.5 |
| 42.15 | 2.14 | 11.2 |
| 43.46 | 2.08 | 13.7 |
| 44.19 | 2.05 | 8.3 |
| 44.55 | 2.03 | 13.1 |
| 45.96 | 1.97 | 16.3 |
| 46.46 | 1.95 | 16.6 |
| 48.33 | 1.88 | 9.4 |
| 49.33 | 1.85 | 9.9 |
| 50.27 | 1.81 | 9.3 |
| 50.48 | 1.81 | 9.9 |
| 51.25 | 1.78 | 8.2 |
| 51.45 | 1.77 | 9.5 |
| 53.86 | 1.70 | 9.1 |
| 55.63 | 1.65 | 9.8 |
| 56.54 | 1.63 | 6.5 |
| 57.53 | 1.60 | 8.8 |
| 59.28 | 1.56 | 6.4 |

Example 5

Alternative Procedure for Preparing Crystalline Form II of 3-Chloro-N-(((3-Chloro-5-Fluorophenyl)Amino)((5-(Trifluoromethyl)-1H-Pyrazol-3-Yl)Amino)Methylene)Benzamide 3-Chloro-N-(((3-chloro-5-fluorophenyl)amino)((5-(trifluoromethyl)-1H-pyrazol-3-yl)amino)methylene)benzamide acetone solvate (176 g) was dissolved in EtOH (875 mL) and warmed to 40° C. The mixture was clarified by filtration through celite and then diluted with EtOH/water (1/1 mixture by volume, 175 mL) at 40° C. Form II crystals of 3-chloro-N-(((3-chloro-5-fluorophenyl)amino)((5-(trifluoromethyl)-

1H-pyrazol-3-yl)amino)methylene)benzamide (437 mg) were added to the mixture. Next, the suspension was further diluted with EtOH/water (1/1 mixture by volume, 700 mL) at 40° C. over 40 minutes, and then the mixture was allowed to cool to room temperature and stirring was continued overnight. Finally, the resulting suspension was filtered, the isolated residue was rinsed with EtOH/water (1/1 mixture by volume, 500 mL) and dried (60° C./10 Torr) to afford 130 g (74% recovery) of 3-chloro-N-(((3-chloro-5-fluorophenyl)amino)((5-(trifluoromethyl)-1H-pyrazol-3-yl)amino)methylene)benzamide as crystalline solid Form II. Analytical analysis did not identify solvate molecules in the crystalline solid.

An X-ray powder diffractogram of the title composition is provided in FIG. 7. A differential scanning calorimetry curve of the title composition is provided in FIG. 8. Tabulated characteristics of the X-ray powder diffractogram in FIG. 7 are provided below in Table 4, which lists diffraction angle 2θ, inter-planar distances d, and relative intensity (expressed as a percentage with respect to the most intense peak).

TABLE 4

X-RAY POWDER DIFFRACTOGRAM DATA.

| Angle [2θ] | d-spacing [Å] | Relative Intensity [%] |
|---|---|---|
| 6.34 | 13.94 | 70.2 |
| 7.32 | 12.06 | 100.0 |
| 9.71 | 9.10 | 23.6 |
| 11.01 | 8.03 | 66.5 |
| 12.74 | 6.95 | 26.9 |
| 13.25 | 6.68 | 16.6 |
| 14.71 | 6.02 | 15.8 |
| 16.05 | 5.52 | 20.3 |
| 16.88 | 5.25 | 39.6 |
| 18.43 | 4.81 | 16.1 |
| 19.17 | 4.63 | 63.4 |
| 19.52 | 4.55 | 14.1 |
| 20.54 | 4.32 | 31.2 |
| 22.15 | 4.01 | 21.3 |
| 22.47 | 3.95 | 11.4 |
| 23.09 | 3.85 | 13.8 |
| 23.64 | 3.76 | 11.4 |
| 23.90 | 3.72 | 14.1 |
| 25.60 | 3.48 | 25.1 |
| 25.93 | 3.43 | 24.0 |
| 27.99 | 3.19 | 15.4 |
| 28.99 | 3.08 | 10.9 |
| 35.61 | 2.52 | 13.2 |

Example 6

Preparation of 3-Chloro-N-(((3-Chloro-5-Fluorophenyl)Amino)((5-(Trifluoromethyl)-1H-Pyrazol-3-Yl)Amino)Methylene-$^{13}$C)Benzamide-1,2,3,4,5,6-$^{13}$C$_6$ The title compound was prepared according to the following procedures.

Part I: Preparation of 3-Chlorobenzoic-1,2,3,4,5,6-$^{13}$C$_6$ Acid

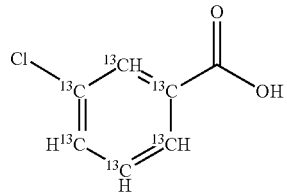

To a solution of 1-chloro-3-iodobenzene-1,2,3,4,5,6-$^{13}$C$_6$ (1 g, 4.1 mmol) in anhydrous tetrahydrofuran (12 mL) at −78° C. under a nitrogen atmosphere was added a 2.0M solution of isopropylmagnesium chloride (2.3 mL, 4.5 mmol) in tetrahydrofuran dropwise over 5 minutes. The resulting mixture was stirred at a temperature of −78° C. for 10 minutes, then carbon dioxide gas was bubbled into solution, keeping a steady stream of carbon dioxide bubbling throughout reaction. Next, the reaction mixture was stirred at −78° C. for 15 minutes, then the reaction vessel was removed from the cooling bath. Once the reaction mixture warmed to ambient temperature, the reaction solution was diluted with diethyl ether (40 mL) and product extracted into 2M sodium hydroxide (3×20 mL). The aqueous extracts were combined and cooled by placing a vessel in an ice bath, and then the aqueous extracts in the cooled vessel were acidified with 6M hydrogen chloride. The product was extracted from the aqueous extracts using diethyl ether (3×20 mL). The organic extracts were combined and washed with brine, dried with magnesium sulfate, filtered, and concentrated to provide the title compound (600 mg, 90%). ESI m/z 161.07, 163.04 (M-H)$^−$.

Part II: Preparation of 3-Chloro-N-((3-chloro-5-fluorophenyl)carbamothioyl-$^{13}$C)benzamide-1,2,3,4,5,6-$^{13}$C$_6$ To a suspension of 3-chlorobenzoic-1,2,3,4,5,6-$^{13}$C$_6$ acid (0.44 g, 2.7 mmol) in anhydrous dichloromethane (10 mL) at 0° C. under a nitrogen atmosphere was added oxalyl chloride (0.34 mL, 4.1 mmol), followed by addition of anhydrous N,N-dimethylformamide (30 μL). Some gas evolution noted. The reaction vessel was removed from the cooling bath, and the reaction mixture was allowed to warm to ambient temperature. Suspended solids in the reaction mixture slowly dissolved. Next, the reaction mixture was stirred at ambient temperature for 2 hours. Then, volatiles were removed in vacuo. The resulting residue was azeotroped with toluene (3×), then with chloroform (3×). The resulting oil was dissolved in acetonitrile (8 mL) to provide a mixture that was cooled with an ice water bath. To the cooled solution was added potassium thiocyanate-$^{13}$C (0.28 g, 2.8 mmol) in a single portion. After 15 minutes, the reaction vessel was removed from the cooling bath and the reaction mixture was stirred at room temperature for 1 hour. To the resulting suspension was added 3-chloro-5-fluoroaniline (0.39 g, 2.7 mmol). After the addition of the aniline, the reaction mixture became very viscous and was diluted with acetonitrile (5 mL). The reaction mixture was stirred at ambient temperature for 1 hour. Then, water (10 mL) was added which caused a solid to form. The solids were filtered off, and then the solids were washed with water and dried in a vacuum oven at 50° C. overnight to provide the title compound (820 mg, 86% yield).

Part III: Preparation of 3-Chloro-N-(((3-chloro-5-fluorophenyl)amino)((5-(trifluoromethyl)-1H-pyrazol-3-yl)amino)methylene-$^{13}$C)benzamide-1,2,3,4,5,6-$^{13}$C$_6$

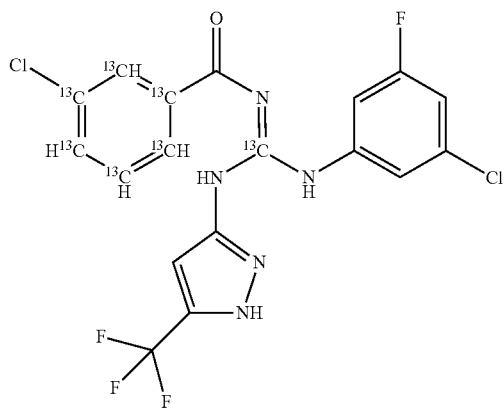 [SMILES: O=C(/N=[13C](/Nc1cc(F)cc(Cl)c1)Nc1cc(C(F)(F)F)[nH]n1)[13c]1[13cH][13cH][13cH][13c](Cl)[13cH]1]

To a suspension of 3-chloro-N-((3-chloro-5-fluorophenyl)carbamothioyl-$^{13}$C)benzamide-1,2,3,4,5,6-$^{13}$C$_6$ (0.77 g, 2.2 mmol) in methyl t-butyl ether (5 mL) at 35° C. was added 5-(trifluoromethyl)-1H-pyrazol-3-amine (0.4 g, 2.6 mmol) followed by N-(3-dimethylaminopropyl)-N'-ethylcarbodiimide hydrochloride (0.65 g, 3.3 mmol). The resulting suspension was stirred for 3 hours at 35° C., during which time the solids were periodically scraped down sides of the reaction vessel. Next, the reaction mixture was partitioned between methyl t-butyl ether and brine, the organic layer was separated and dried with sodium sulfate, filtered through celite, then concentrated onto coarse silica. The mixture was purified by column chromatography eluting with a gradient of 0% to 10% v/v ethyl acetate in hexanes to provide the title compound (320 mg, 30% yield).

Example 7

Preparation of 4-Chloro-N-((3-Chloro-5-Fluorophenyl)Carbamothioyl)Benzamide

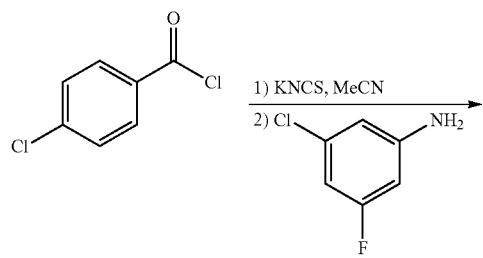

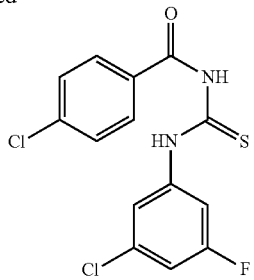

4-Chlorobenzoyl chloride (10.2 g, 58.5 mmol) was dissolved in acetonitrile (230 mL) and the reaction vessel containing this mixture was cooled in an ice/water bath. To this mixture was added potassium thiocyanate (6.25 g, 64.4 mol, 1.10 equiv). The cooling bath was removed from the reaction vessel after 15 minutes and the resulting reaction slurry was stirred at room temperature for approximately 1 hour. 3-Chloro-5-fluoroaniline (7.05 mL, 70.2 mol, 1.2 equiv) was added as a solution in acetonitrile (7 mL) over 5 minutes to the reaction mixture. Next, the reaction mixture was stirred at room temperature overnight and then quenched with water (230 mL), and the resulting mixture was stirred at room temperature for 1 hour. The mixture was filtered to collect the solids, the isolated solids were rinsed with acetonitrile/water (1/1 mixture by volume, 50 mL), and the resulting solid was dried at 60° C. in vacuo to provide 20.5 g the title compound as a solid. $^1$H NMR (DMSO-d$_6$) of the title compound: δ 12.5 (s, 1H), 11.8 (s, 1H), 8.01 (t, 1H, J=1.8), 7.96 (d, 2H, J=8.6), 7.67 (m, 2H), 7.59 (d, 2H, J=8.6), 7.33 (d, 1H, J=8.4). HPLC: >99% purity at 23.52 min.

Example 8

Preparation of 4-Chloro-N-(((3-Chloro-5-Fluorophenyl)Amino)((5-(Trifluoromethyl)-1H-Pyrazol-3-Yl)Amino)Methylene)Benzamide

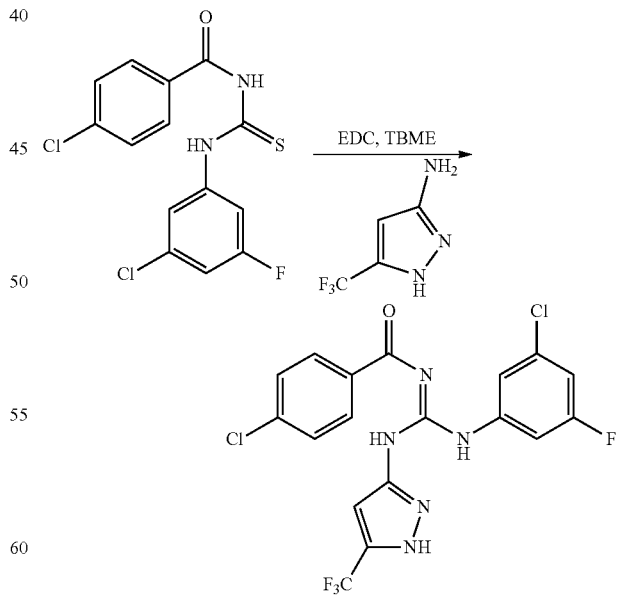

A suspension of 4-chloro-N-((3-chloro-5-fluorophenyl)carbamothioyl)benzamide (20.5 g, 59.7 mmol) in TBME (500 mL) was heated to 50° C. 5-(Trifluoromethyl)-1H-pyrazol-3-amine (10.8 g, 71.7 mmol, 1.20 equiv) and N-(3-dimethylaminopropyl)-N'-ethylcarbodiimide (EDC) (17.6 g, 89.6 mmol, 1.50 equiv) were added. The resulting reaction mixture was stirred at 40° C. for 3 hr and then diluted with a saturated aqueous sodium chloride solution (0.5 L). The organic layer of the resulting mixture was isolated, dried ($Na_2SO_4$), filtered, and concentrated. The resulting residue was diluted with EtOAc (20 mL), and this mixture was warmed to 50° C., then diluted with heptane (20 mL). Next, the heat source was removed and the mixture was allowed to cool to room temperature, then an ice/water bath was applied to the reaction vessel to affect precipitation. The resulting solids were collected by filtration, rinsed with EtOAc/heptane (1/1 mixture by volume, 20 mL) and air dried at room temperature. Then, the solids were dissolved in EtOH (80 mL) and the resulting mixture warmed to 40° C. EtOH/water (1/1 mixture by volume, 80 mL) was added to the mixture slowly over 40 minutes. Then, the heat source was removed from the reaction vessel and the reaction mixture was allowed to stir at room temperature for 2 days. Then, the reaction mixture was filtered, collected solids were rinsed with EtOH/water (1/1 mixture by volume, 15 mL), and dried (60° C./10 Torr) to afford the title compound (15.2. g, 57% yield). $^1$H NMR (DMSO-$d_6$) of the title compound: δ 13.3 (s, 1H), 10.7 (s, 1H), 10.0 (s, 1H), 7.90 (s, 1H), 7.90 (d, 2H, J=8.4), 7.72 (d, 1H, J=11.5), 7.63 (m, 3H), 7.07 (d, 1H, J=8.5), 6.00 (s, 1H). HPLC: 98.6% purity at 26.02 min.

Example 9

Biological Activity Towards ATPase and Ramos Cells

Exemplary compounds were tested for activity against $F_1F_0$-ATPase and Ramos cells. Experimental procedures and results are described below.

Part I

Compounds in Table 5 below were tested for activity against $F_1F_0$-ATPase by measuring the ability of the compounds to inhibit ATP synthesis. In addition, the compounds were assessed for cytotoxicity in Ramos cells. Results of the biological activity tests are shown in Table 5 below. Inhibition of $F_1F_0$-ATPase activity in synthesizing ATP and cytotoxicity in Ramos cells were measured according to the procedures described in K. M. Johnson et al. *Chemistry & Biology* 2005, 12, 485-496.

TABLE 5

| Compound No. | Compound Structure | ATP Syn IC$_{50}$ (μM) | Ramos Cell EC$_{50}$ (μM) |
|---|---|---|---|
| 1 | Crystalline Form I of 3-chloro-N-(((3-chloro-5-fluorophenyl)amino)((5-(trifluoromethyl)-1H-pyrazol-3-yl)amino)methylene)benzamide | 0.04 | 0.05 |
| 2 | [structure] | 0.09 | 0.1 |
| 3 | [structure] | 0.31 | 1.84 |
| 4 | [structure] | 0.04 | 0.12 |

Part II

The activity of compound 3-chloro-N-(((3-chloro-5-fluorophenyl)amino)((5-(trifluoromethyl)-1H-pyrazol-3-yl)amino)methylene)benzamide towards $F_1F_0$-ATPase and Ramos cells was evaluated by performing multiple times the assay procedures described in Part I. In particular, activity against $F_1F_0$-ATPase was evaluated by measuring the ability of the compound to inhibit ATP synthesis in twelve independent experiments. Cytotoxicity towards Ramos cells was measured in thirteen independent experiments. Consistent with the procedure in Part I, the compound was dissolved in dimethylsulfoxide to form a solution that was applied to $F_1F_0$-ATPase or Ramos cells, and the assays were performed according to procedures described in K. M. Johnson et al. *Chemistry & Biology* 2005, 12, 485-496.

$IC_{50}$ values (for inhibition of $F_1F_0$-ATPase activity in synthesizing ATP) from multiple replications of the experimental procedure were averaged. The mean $IC_{50}$ value for 3-chloro-N-(((3-chloro-5-fluorophenyl)amino)((5-(trifluoromethyl)-1H-pyrazol-3-yl)amino)methylene)benzamide for inhibition of $F_1F_0$-ATPase activity in synthesizing ATP was determined to be 27±1.7 nM.

Similarly, $EC_{50}$ values (for cytotoxicity towards Ramos cells) from multiple replications of the experimental procedure were averaged. The mean $EC_{50}$ value for 3-chloro-N-(((3-chloro-5-fluorophenyl)amino)((5-(trifluoromethyl)-1H-pyrazol-3-yl)amino)methylene)benzamide for cytotoxicity towards Ramos cells was determined to be 59±6 nM.

Example 10

Inhibition of Cytochrome P450 2D6

Compounds in Table 6 below were tested for activity against Cytochrome P450 2D6 (hereinafter "CYP2D6"). Procedures and results are described below.

Part I—Test Procedure:

Master solutions were prepared containing human liver microsomes (Gibco, 0.2 mg/mL) and $MgCl_2$ (5 mM) in potassium phosphate buffer (10 mM). To aliquots (169 μL) of the microsome solution was added test compound in acetonitrile (1 μL) and DMSO (1 μL) to provide final test compound concentrations of 0, 0.005, 0.05, 0.25, 1, 5, 10, and 25 μM.

NADPH (10 mM) in ultra-pure water (20 μL) was added, and this mixture was incubated at 37° C. for 30 minutes. The enzyme reaction then was initiated by the addition of enzyme substrate (dextromethorphan) dissolved in 1 μL of acetonitrile and 9 μL of ultra-pure water. The final substrate concentration was 10 μM.

After 20 minutes, the incubation mixture was diluted with 3 volumes of cold methanol containing imipramine (200 nM), labetalol (200 nM), and ketoprofen (2 μM) as internal standards. Samples were centrifuged at 16,000 g for 10 minutes, then an aliquot of the supernatant (200 μL) was removed and analyzed by LC/MS/MS.

LC/MS/MS analyses were performed in duplicate using a Shimadzu HPLC and an API 4000 mass spectrometer. Liquid chromatography employed a Phenomenex C18, 5 μm, 50×2 mm column fitted with a guard column. Solvent A was acetonitrile containing 0.1% v/v formic acid. Solvent B was water containing 0.1% v/v formic acid. Elution was performed at 0.5 mL per minute: 0-2 min, gradient of 5% Solvent A/95% Solvent B to 100% Solvent A; 2.0-2.2 min, 100% Solvent A; 2.2-2.4 min, gradient of 100% Solvent A to 5% Solvent A/95% Solvent B; 2.4-3.0 min, Solvent 5% A/Solvent B 95%.

The formation of metabolites was evaluated by peak area, and data were analyzed using Prism 5.0 software (GraphPad). The amount of metabolite formed compared to a control sample containing no test compound was plotted as a function of test compound concentration.

The $IC_{50}$ value of the test compound was determined from the plot as the concentration at which the test compound confers 50% inhibition of metabolite formation.

Part II—Results:

$IC_{50}$ inhibition values for Compound 1 and Compound 2 are provided in Table 6. Compound 1 was approximately three-fold less potent in inhibiting CYP2D6 compared to Compound 2 in the experiment.

TABLE 6

Inhibition of CYP2D6 Thirty Minutes After Administration of Test Compound.

| Compound No. | Compound Structure | CYP2D6 $IC_{50}$ (μM) |
|---|---|---|
| 1 | Crystalline Form I of 3-chloro-N-(((3-chloro-5-fluorophenyl)amino)((5-(trifluoromethyl)-1H-pyrazol-3-yl)amino)methylene)benzamide | 3.2 |
| 2 | 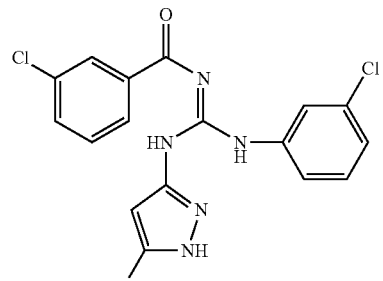 | 1.1 |

Incorporation by Reference

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:
1. A compound represented by Formula I:

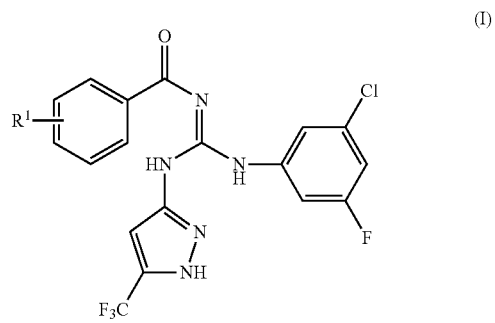

or a geometric isomer or tautomer; or a pharmaceutically acceptable salt or solvate of any of the foregoing; wherein $R^1$ is a chloro group located at either the meta-position or para-position of the phenyl group to which it is attached.

2. The compound of claim 1, wherein the compound is a compound of Formula I or a geometric isomer or tautomer, or a pharmaceutically acceptable salt of any of the foregoing.

3. The compound of claim 1, wherein the compound is in the form of a solvate.

4. The compound of claim 1, wherein the compound is represented by:

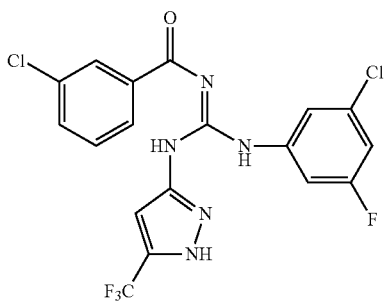 [SMILES: O=C(/N=C(/Nc1cc(F)cc(Cl)c1)Nc1cc(C(F)(F)F)[nH]n1)c1cccc(Cl)c1]

or a geometric isomer or tautomer; or a pharmaceutically acceptable salt of any of the foregoing.

5. The compound of claim 1, wherein the compound is represented by:

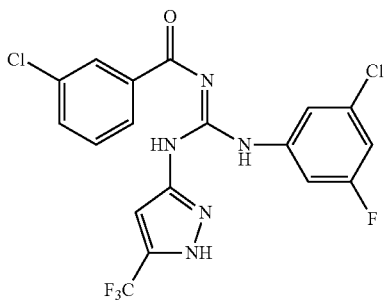 [SMILES: O=C(/N=C(/Nc1cc(F)cc(Cl)c1)Nc1cc(C(F)(F)F)[nH]n1)c1cccc(Cl)c1]

or a geometric isomer or tautomer; or a solvate of any of the foregoing.

6. The compound of claim 5, wherein the compound is in the form of an acetone solvate.

7. The compound of claim 1, wherein the compound is represented by:

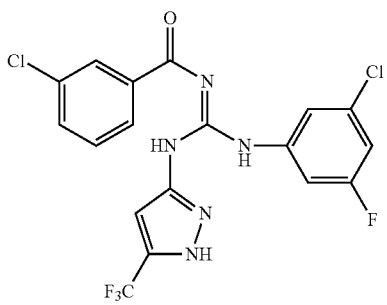 [SMILES: O=C(/N=C(/Nc1cc(F)cc(Cl)c1)Nc1cc(C(F)(F)F)[nH]n1)c1cccc(Cl)c1]

or a geometric isomer or tautomer.

8. The compound of claim 1, wherein the compound is represented by:

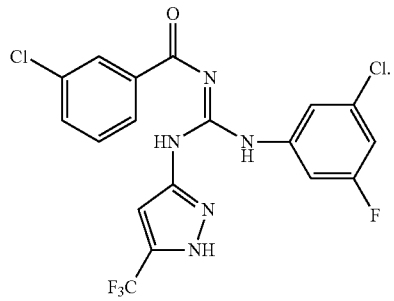 [SMILES: O=C(/N=C(/Nc1cc(F)cc(Cl)c1)Nc1cc(C(F)(F)F)[nH]n1)c1cccc(Cl)c1]

9. Crystalline compound 3-chloro-N-(((3-chloro-5-fluorophenyl)amino)((5-(trifluoromethyl)-1H-pyrazol-3-yl)amino)methylene)benzamide.

10. The crystalline compound of claim 9, wherein the crystalline compound exhibits an X-ray powder diffraction pattern comprising peaks at the following diffraction angles (2θ): 6.2±0.2, 7.1±0.2, 9.4±0.2, 10.7±0.2, 15.6±0.2, 19.0±0.2, 20.0±0.2, and 25.2±0.2.

11. The crystalline compound of claim 10, wherein the relative intensity of the peak at said diffraction angles (2θ) is at least 30%.

12. The crystalline compound of claim 10 characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
| --- | --- | --- |
| 6.2 | 14.3 | 53.8 |
| 7.1 | 12.4 | 69.6 |
| 9.4 | 9.4 | 53.8 |
| 10.7 | 8.3 | 51.0 |
| 12.9 | 6.9 | 34.6 |
| 15.6 | 5.7 | 92.8 |
| 16.4 | 5.4 | 29.1 |
| 17.9 | 4.9 | 44.0 |
| 19.0 | 4.7 | 100.0 |
| 20.0 | 4.4 | 62.6 |
| 21.9 | 4.1 | 38.9 |
| 23.6 | 3.8 | 51.4 |
| 25.2 | 3.5 | 57.8 |
| 27.3 | 3.3 | 24.0 |
| 28.4 | 3.1 | 15.8 |
| 35.0 | 2.6 | 10.0. |

13. The crystalline compound of claim 10, wherein the X-ray powder diffraction pattern is substantially as shown in FIG. 3.

14. The crystalline compound of claim 11, wherein the crystalline compound has a melting point onset as determined by differential scanning calorimetry in the range of from about 157 degrees Celsius to about 161 degrees Celsius.

15. The crystalline compound of claim 11, wherein the crystalline compound has a melting point onset as determined by differential scanning calorimetry at about 159 degrees Celsius.

16. The crystalline compound of claim 11, wherein the crystalline compound has a differential scanning calorimetry curve substantially the same as shown in FIG. 4.

17. The crystalline compound of claim 9, wherein the crystalline compound exhibits an X-ray powder diffraction pattern comprising peaks at the following diffraction angles (2θ): 6.3±0.2, 7.3±0.2, 11.0±0.2, 12.8±0.2, 16.9±0.2, 19.2±0.2, 20.6±0.2, 22.2±0.2, 25.7±0.2, 26.0±0.2, and 35.7±0.2.

18. The crystalline compound of claim 17, wherein the relative intensity of the peak at said diffraction angles (2θ) is at least 15%.

19. The crystalline compound of claim 17 characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
| --- | --- | --- |
| 6.33 | 13.95 | 65.8 |
| 7.32 | 12.06 | 100.0 |
| 9.73 | 9.08 | 14.8 |
| 11.03 | 8.01 | 55.9 |
| 12.76 | 6.93 | 18.3 |
| 13.27 | 6.67 | 9.7 |
| 14.75 | 6.00 | 9.3 |
| 16.07 | 5.51 | 12.7 |
| 16.91 | 5.24 | 27.2 |
| 18.45 | 4.80 | 9.9 |
| 19.18 | 4.62 | 42.0 |
| 19.53 | 4.54 | 8.3 |
| 20.56 | 4.31 | 19.8 |
| 22.20 | 4.00 | 88.4 |
| 22.51 | 3.95 | 43.5 |
| 23.11 | 3.85 | 56.1 |
| 23.55 | 3.77 | 29.0 |
| 25.65 | 3.47 | 48.8 |
| 25.96 | 3.43 | 100.0 |
| 26.75 | 3.33 | 26.2 |
| 28.03 | 3.18 | 52.6 |
| 29.03 | 3.07 | 44.7 |
| 29.51 | 3.02 | 29.3 |
| 30.45 | 2.93 | 20.0 |
| 31.49 | 2.84 | 17.8 |
| 31.82 | 2.81 | 20.4 |
| 32.27 | 2.77 | 29.9 |
| 33.15 | 2.70 | 16.8 |
| 34.18 | 2.62 | 12.9 |
| 35.66 | 2.52 | 59.6 |
| 36.03 | 2.49 | 17.7 |
| 36.84 | 2.44 | 13.5 |
| 37.75 | 2.38 | 14.8 |
| 38.27 | 2.35 | 10.9 |
| 38.99 | 2.31 | 13.6 |
| 39.71 | 2.27 | 13.5 |
| 42.15 | 2.14 | 11.2 |
| 43.46 | 2.08 | 13.7 |
| 44.19 | 2.05 | 8.3 |
| 44.55 | 2.03 | 13.1 |
| 45.96 | 1.97 | 16.3 |
| 46.46 | 1.95 | 16.6 |
| 48.33 | 1.88 | 9.4 |
| 49.33 | 1.85 | 9.9 |
| 50.27 | 1.81 | 9.3 |
| 50.48 | 1.81 | 9.9 |
| 51.25 | 1.78 | 8.2 |
| 51.45 | 1.77 | 9.5 |
| 53.86 | 1.70 | 9.1 |
| 55.63 | 1.65 | 9.8 |
| 56.54 | 1.63 | 6.5 |
| 57.53 | 1.60 | 8.8 |
| 59.28 | 1.56 | 6.4. |

20. The crystalline compound of claim 17, wherein the X-ray powder diffraction pattern is substantially as shown in FIG. 5.

21. The crystalline compound of claim 18, wherein the crystalline compound has a melting point onset as determined by differential scanning calorimetry in the range of from about 158 degrees Celsius to about 165 degrees Celsius.

22. The crystalline compound of claim 18, wherein the crystalline compound has a differential scanning calorimetry curve substantially the same as shown in FIG. 6.

23. The crystalline compound 3-chloro-N-(((3-chloro-5-fluorophenyl)amino)((5-(trifluoromethyl)-1H-pyrazol-3-yl)amino)methylene)benzamide acetone solvate exhibiting an X-ray powder diffraction pattern comprising peaks at the following diffraction angles (2θ): 6.2±0.2, 8.3±0.2, 14.7±0.2, 17.5±0.2, 17.9±0.2, 18.5±0.2, 20.2±0.2, 20.9±0.2, 23.5±0.2, and 25.9±0.2.

24. The crystalline compound of claim 23, wherein the relative intensity of the peak at said diffraction angles (2θ) is at least 15%.

25. The crystalline compound of claim 23 characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
| --- | --- | --- |
| 6.2 | 14.3 | 100 |
| 7.2 | 12.3 | 14.4 |
| 8.3 | 10.7 | 54.6 |
| 14.7 | 6.0 | 32.6 |
| 15.7 | 5.6 | 12.6 |
| 15.8 | 5.6 | 16.2 |
| 16.8 | 5.3 | 13.5 |
| 17.5 | 5.1 | 39.7 |
| 17.9 | 5.0 | 20.7 |
| 18.5 | 4.8 | 23.3 |
| 19.0 | 4.7 | 23.0 |
| 19.6 | 4.5 | 11.4 |
| 20.1 | 4.4 | 18.1 |
| 20.2 | 4.4 | 23.5 |
| 20.4 | 4.3 | 10.8 |
| 20.9 | 4.3 | 31.0 |
| 21.9 | 4.1 | 11.9 |
| 23.5 | 3.8 | 20.2 |
| 23.7 | 3.7 | 13.4 |
| 24.1 | 3.7 | 12.2 |
| 24.4 | 3.7 | 21.0 |
| 24.6 | 3.6 | 16.0 |
| 25.3 | 3.5 | 13.4 |
| 25.9 | 3.4 | 60.9 |
| 26.5 | 3.4 | 12.9 |
| 27.9 | 3.2 | 10.9 |
| 28.1 | 3.2 | 11.9 |
| 29.1 | 3.1 | 14.0. |

26. The crystalline compound of claim 23, wherein the X-ray powder diffraction pattern is substantially as shown in FIG. 1.

27. The crystalline compound of claim 24, wherein the crystalline compound has a melting point onset as determined by differential scanning calorimetry at about 159 degrees Celsius.

28. The crystalline compound claim 24, wherein the crystalline compound has a differential scanning calorimetry curve substantially the same as shown in FIG. 2.

29. A pharmaceutical composition comprising a compound of claim 1 and a pharmaceutically acceptable carrier.

30. A pharmaceutical composition comprising a compound of claim 4 and a pharmaceutically acceptable carrier.

31. A pharmaceutical composition comprising a compound of claim 5 and a pharmaceutically acceptable carrier.

32. A pharmaceutical composition comprising a compound of claim 7 and a pharmaceutically acceptable carrier.

33. A pharmaceutical composition comprising a crystalline compound of claim 9 and a pharmaceutically acceptable carrier.

34. A pharmaceutical composition comprising a crystalline compound of claim 10 and a pharmaceutically acceptable carrier.

35. A pharmaceutical composition comprising a crystalline compound of claim 17 and a pharmaceutically acceptable carrier.

36. A pharmaceutical composition comprising a crystalline compound of claim 18 and a pharmaceutically acceptable carrier.

37. A method of treating a disorder selected from the group consisting of an immune disorder, inflammatory disorder, cardiovascular disease, myeloma, lymphoma, cancer, and bacterial infection, comprising administering to a patient in need thereof a therapeutically effective amount of a compound of claim 1 in order to ameliorate a symptom of the disorder.

38. The method of claim 37, wherein the disorder is rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, uveitis, or epidermal hyperplasia.

39. The method of claim 37, wherein the disorder is Crohn's disease or ulcerative colitis.

40. The method of claim 37, wherein the disorder is cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, or autoimmune hepatitis.

41. The method of claim 37, wherein the patient is a human.

42. A method of inhibiting a $F_1F_0$-ATPase, comprising exposing a $F_1F_0$-ATPase to a compound of claim 1 to inhibit said $F_1F_0$-ATPase.

43. The method of claim 42, wherein the $F_1F_0$-ATPase is mitochondrial $F_1F_0$-ATPase.

44. The method of claim 37, wherein the compound is

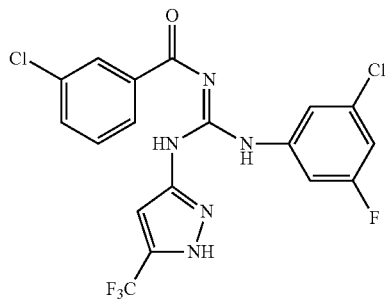 [SMILES: O=C(/N=C(/Nc1cc(F)cc(Cl)c1)Nc1cc(C(F)(F)F)[nH]n1)c1cccc(Cl)c1]

or a geometric isomer or tautomer; or pharmaceutically acceptable salt of any of the foregoing.

45. The method of claim 37, wherein the compound is

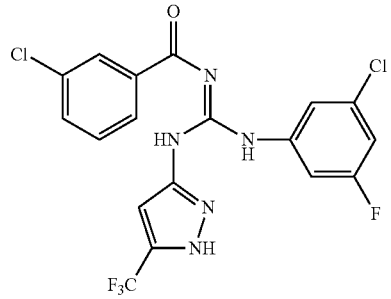 [SMILES: O=C(/N=C(/Nc1cc(F)cc(Cl)c1)Nc1cc(C(F)(F)F)[nH]n1)c1cccc(Cl)c1]

or a geometric isomer or tautomer.

46. The method of claim 37, wherein the compound is crystalline 3-chloro-N-(((3-chloro-5-fluorophenyl)amino) ((5-(trifluoromethyl)-1H-pyrazol-3-yl)amino)methylene) benzamide.

47. The method of claim 37, wherein the compound is crystalline 3-chloro-N-(((3-chloro-5-fluorophenyl)amino) ((5-(trifluoromethyl)-1H-pyrazol-3-yl)amino)methylene) benzamide wherein the crystalline compound exhibits an X-ray powder diffraction pattern comprising peaks at the following
diffraction angles (2θ): 6.2±0.2, 7.1±0.2, 9.4±0.2, 10.7±0.2, 15.6±0.2, 19.0±0.2, 20.0±0.2, and 25.2±0.2.

48. The method of claim 37, wherein the compound is crystalline 3-chloro-N-(((3-chloro-5-fluorophenyl)amino) ((5-(trifluoromethyl)-1H-pyrazol-3-yl)amino)methylene) benzamide wherein the crystalline compound exhibits an X-ray powder diffraction pattern comprising peaks at the following
diffraction angles (2θ): 6.3±0.2, 7.3±0.2, 11.0±0.2, 12.8±0.2, 16.9±0.2, 19.2±0.2, 20.6±0.2, 22.2±0.2, 25.7±0.2, 26.0±02, and 35.7±0.2.

49. The method of claim 39, wherein the compound is

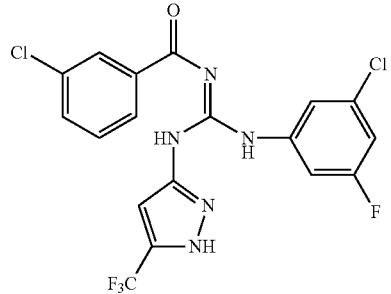 [SMILES: O=C(/N=C(/Nc1cc(F)cc(Cl)c1)Nc1cc(C(F)(F)F)[nH]n1)c1cccc(Cl)c1]

or a geometric isomer or tautomer; or pharmaceutically acceptable salt of any of the foregoing.

50. The method of claim 39, wherein the compound is

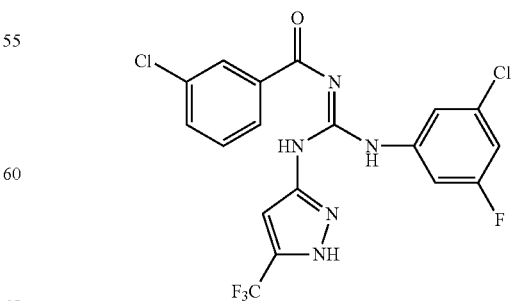

or a geometric isomer or tautomer.

51. The method of claim 39, wherein the compound is crystalline 3-chloro-N-(((3-chloro-5-fluorophenyl)amino)((5-(trifluoromethyl)-1H-pyrazol-3-yl)amino)methylene)benzamide.

52. The method of claim 39, wherein the compound is crystalline 3-chloro-N-(((3-chloro-5-fluorophenyl)amino)((5-(trifluoromethyl)-1H-pyrazol-3-yl)amino)methylene)benzamide wherein the crystalline compound exhibits an X-ray powder diffraction pattern comprising peaks at the following
diffraction angles (2θ): 6.2±0.2, 7.1±0.2, 9.4±0.2, 10.7±0.2, 15.6±0.2, 19.0±0.2, 20.0±0.2, and 25.2±0.2.

53. The method of claim 39, wherein the compound is crystalline 3-chloro-N-(((3-chloro-5-fluorophenyl)amino)((5-(trifluoromethyl)-1H-pyrazol-3-yl)amino)methylene)benzamide wherein the crystalline compound exhibits an X-ray powder diffraction pattern comprising peaks at the following
diffraction angles (2θ): 6.3±0.2, 7.3±0.2, 11.0±0.2, 12.8±0.2, 16.9±0.2, 19.2±0.2, 20.6±0.2, 22.2±0.2, 25.7±0.2, 26.0±0.2, and 35.7±0.2.

\* \* \* \* \*